United States Patent
Tsuchida et al.

(10) Patent No.: US 6,323,383 B1
(45) Date of Patent: Nov. 27, 2001

(54) SYNTHESIS METHOD OF CHEMICAL INDUSTRIAL RAW MATERIAL AND HIGH-OCTANE FUEL, AND HIGH-OCTANE FUEL COMPOSITION

(75) Inventors: Takashi Tsuchida; Kiminori Atsumi; Shuji Sakuma, all of Tokyo; Tomoyuki Inui, Uji, all of (JP)

(73) Assignee: Kabushiki Kaisha Sangi (JP)

(*) Notice: Subject to any disclaimer, the term of this patent is extended or adjusted under 35 U.S.C. 154(b) by 0 days.

(21) Appl. No.: 09/601,139

(22) PCT Filed: Jan. 28, 1999

(86) PCT No.: PCT/JP99/00347

§ 371 Date: Sep. 27, 2000

§ 102(e) Date: Sep. 27, 2000

(87) PCT Pub. No.: WO99/38822

PCT Pub. Date: Aug. 5, 1999

(30) Foreign Application Priority Data

Jan. 30, 1998 (JP) .................................................. 10/032284

(51) Int. Cl.[7] .............................. C01L 1/18; C07C 11/00
(52) U.S. Cl. .......................... 585/601; 585/627; 585/632; 44/300; 44/451; 568/902.2
(58) Field of Search ..................................... 585/601, 627, 585/632; 44/300, 451; 568/902.2

(56) References Cited

U.S. PATENT DOCUMENTS 4,232,179    11/1980   Barrocas et al. .
5,723,401  * 3/1998    Sakuma et al. ....................... 502/213

FOREIGN PATENT DOCUMENTS

| 151583 | 3/1942 | (JP) . |
| 55-178281 | 6/1982 | (JP) . |
| 56-157814 | 4/1983 | (JP) . |
| 5-305238 | 11/1993 | (JP) . |
| 8-127783 | 5/1996 | (JP) . |

OTHER PUBLICATIONS

S.K. Bhattacharyya et al., "One–Step Catalytic Conversion of Ethanol to Butadiene in the Fixed Bed ll*. Binary— and Ternary–Oxide Catalysts", J. Appl. Chem.; Mar. 12, 1962, pp. 105–110.

* cited by examiner

Primary Examiner—Margaret Medley
Assistant Examiner—Cephia D. Toomer
(74) Attorney, Agent, or Firm—Parkhurst & Wendel, L.L.P.

(57) ABSTRACT

A process for the synthesis of chemical industrial feedstock and high-octane fuel, wherein calcium phosphate which is controlled in the molar Ca/P ratio and/or one which contains an activating metal (M) at a molar (Ca+M)/P ratio of 1 to 2 is used as the catalyst and ethanol is used as the feedstock.

4 Claims, 3 Drawing Sheets

Figure 1:
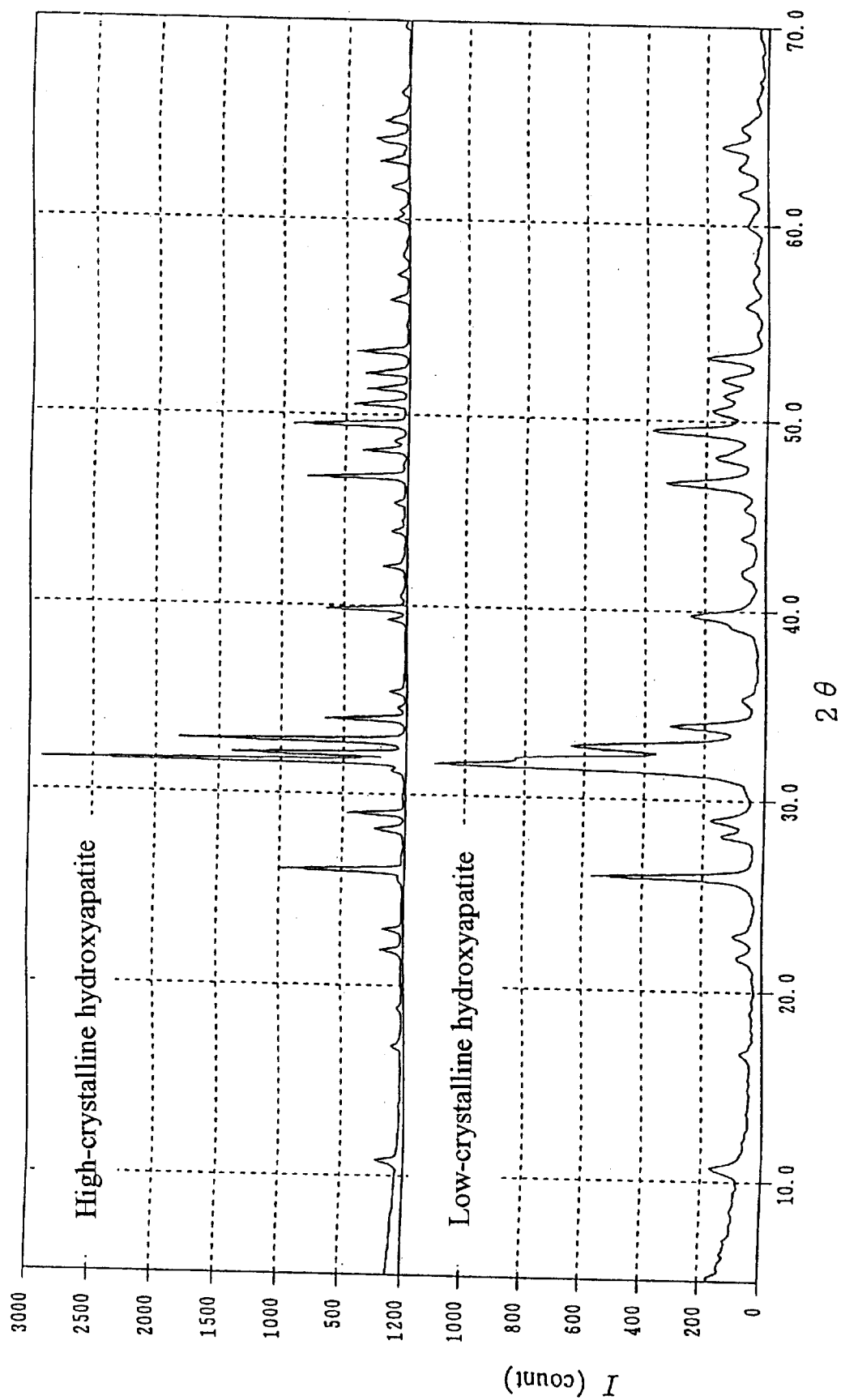

SYNTHESIS METHOD OF CHEMICAL INDUSTRIAL RAW MATERIAL AND HIGH-OCTANE FUEL, AND HIGH-OCTANE FUEL COMPOSITION

This application is a 371 of PCT/JP 99/00347, filed Jan. 28, 1999.

TECHNICAL FIELD

The present invention relates to a method of producing chemical industrial raw materials, a high-octane fuel, and a mixture thereof from ethanol by using calcium phosphate or calcium phosphate carrying thereon a metal as a catalyst.

BACKGROUND OF THE INVENTION

Recently, an attempt of supplying a large amount of chemical industrial raw materials by using alcohols, in particular, ethanol as the raw material in place of chemical industrial raw materials induced from petroleum as been widely noticed.

A method of producing ethylene from ethanol as the raw material wherein calcium phosphate is used as a catalyst is known but the method shows a low activity and is economically disadvantageous. Also, as a dehydration method of an alcohol, the use of a solid acid catalyst such as zeolite, etc., is known but in the method, aluminum in the zeolite structure is released by the action of water formed by the reaction, which results in lowering the catalyst activity, and the method cannot be industrially used for a long period of time.

A method of producing acetaldehyde from ethanol by using calcium phosphate or calcium phosphate carrying a metal such as Cu, Ni, etc. is known but the activity and the selectivity are low, and the method is economically disadvantageous. Also, as a dehydration method of ethanol, a solid base catalyst such as a carrier-type platinum-group catalyst, MgO, etc., is known but there are problems in the point of the dispersion of the characteristics with impurities and the stability.

As a method of producing diethyl ether from ethanol, a solid acid catalyst such as zeolite, etc., is known but aluminum in the zeolite structure is released by water formed by the reaction, whereby the catalyst activity is lowered and the catalyst cannot be used for a long period of time.

As a method of producing 1,3-butadiene from ethanol, a method of using $Al_2O_3 \cdot ZnO$ (6:4) as a catalyst [S. K. Bhattacharyya and N. O. Ganguly; J. Appl. Chem.; 12, 105(1962)] and a method of using sepiolite adsorbed with a metal (Mn, V, Mo. W. etc.) (Japanese Patent Application Nos. 178281/1980and 157814/1981) are proposed. However, in the former method, there are problems about a method of stably producing the catalyst and the thermal stability of the catalyst itself, and the latter method is the result in a batch test level and thus in the method, there is a problem in the point of a mass production. Accordingly, 1,3-butadiene is generally produced from a fossil fuel containing butenes. As an industrial synthesis method of 1-butanol, an acetaldehyde method, a Reppe method, etc., are known but these methods are complicated and poor in efficiency. Japanese Patent Laid-Open Publication No. 305238/1993 discloses a method of obtaining gasoline-base hydrocarbons from lower alcohols using a catalyst formed by carrying a metal on a calcium phosphate-base compound.

DISCLOSURE OF THE INVENTION

An object of the present invention is to provide a production method for efficiently obtaining chemical industrial raw materials such as ethylene, acetaldehyde, diethyl ether, 1-butanol, 1,3-butadiene, etc., a high-octane fuel, and a mixture thereof using ethanol as the raw material.

As the result of detailed investigations on the method of obtaining chemical industrial raw materials such as ethylene, acetaldehyde, diethyl ether, 1-butanol, 1,3-butadiene, etc., and a high-octane fuel, etc., using ethanol as the raw material by an industrially advantageous method, the present invention has found that the above-described object can be attained by using a calcium phosphate-base catalyst.

BRIEF DESCRIPTION OF THE INVENTION

Figure 2:
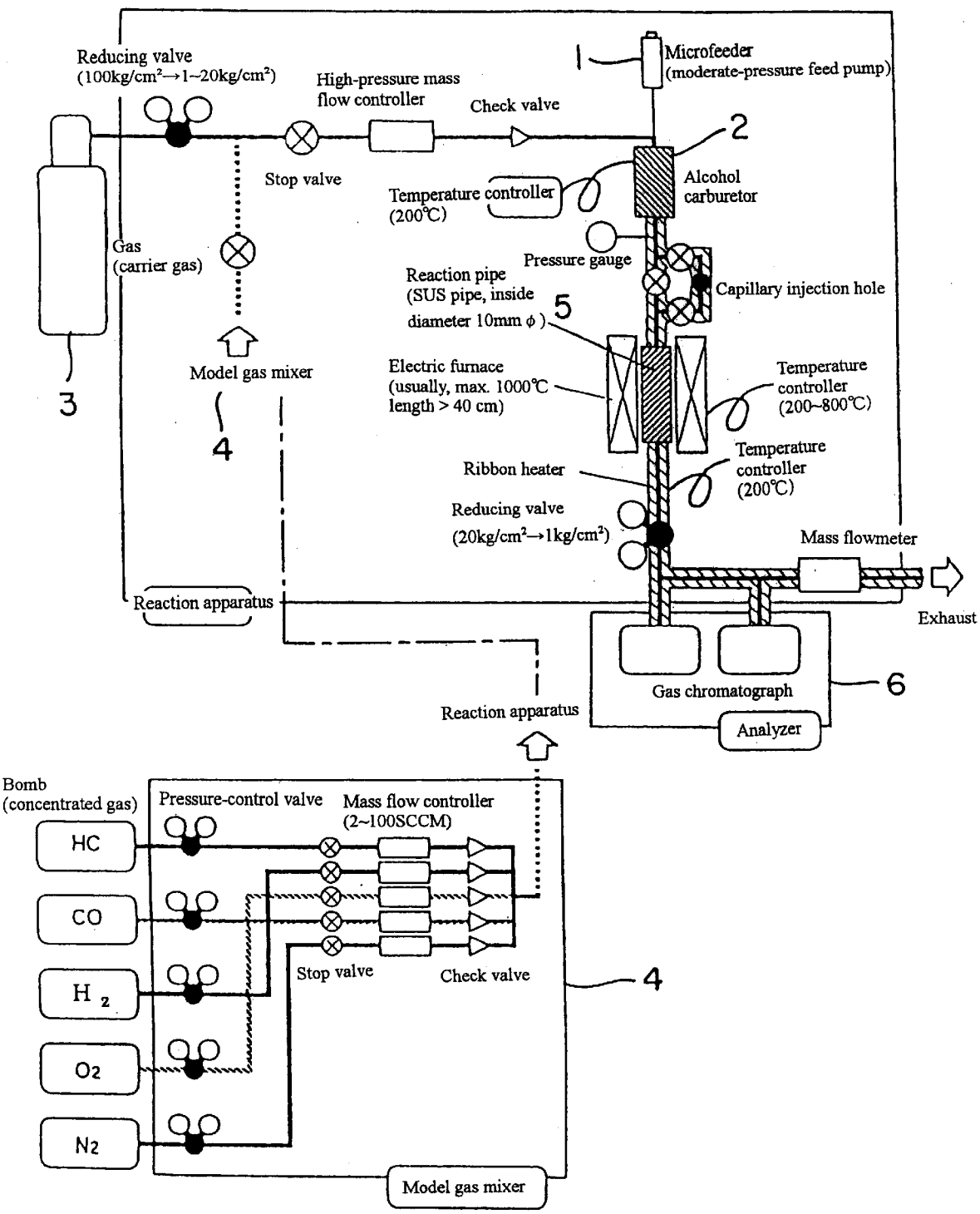
Figure 3:
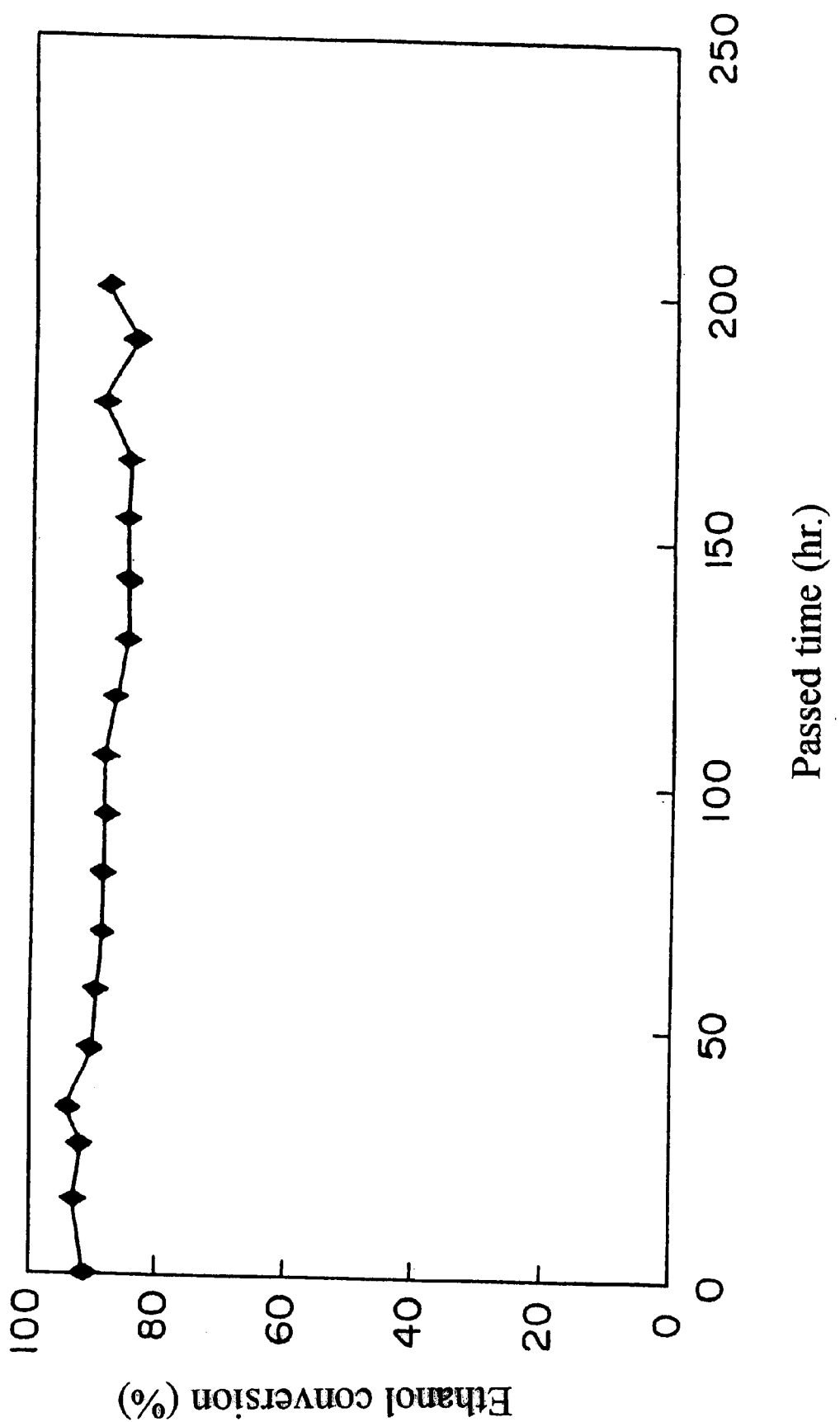

FIG. 1 is a graph showing the X-ray diffraction patterns of a high-crystalline powder and a low-crystalline powder, FIG. 2 is a view showing the reaction apparatus used in the example of the invention, and FIG. 3 is a view showing the relation between the reaction time of a catalyst repeating a regeneration treatment and the ethanol conversion.

BEST MODE FOR CARRYING OUT THE INVENTION

Then, the invention is described in detail.

As calcium phosphate, the existences of hydroxyapatite $[Ca_{10}(PO_4)_6(OH)_2]$, calcium tertiary phosphate $[Ca_3(PO_4)_2]$, calcium hydrogen phosphate $[CaHPO_4 \cdot (0 \text{ to } 2)H_2O]$, calcium diphosphate $(Ca_2P_2O_7)$, octacalcium dihydrogen phosphate $[Ca_8H_2(PO4)_6 \cdot 5H_2O]$, tetracalcium phosphate $[Ca_4(PO_4)_2O]$, amorphous calcium phosphate $[Ca_3(PO_4)_2 \cdot nH_2O]$, etc., are known.

Hydroxyapatite is usually shown by the above-described stoichiometric composition but the feature thereof is that even when the composition does not satisfy the stoichiometric composition, hydroxyapatite can take an apatite structure. The hydroxyapatite of such a non-stoichiometric composition can be shown by $[Ca_{10-z}(HPO_4)_z(PO4)_{6-z}(OH)_{2-z} \cdot nH_2O$ $\{0<z \leq 1, n=0 \text{ to } 2.5\}]$.

Also, amorphous calcium phosphate is calcium phosphate which is halo in the X-ray diffraction.

A low-crystalline powder in the invention is a low-crystalline powder the X-ray diffraction peak of which is broad as compared with that of a high-crystalline powder. For example, using hydroxyapatite, the X-ray diffraction patterns of the high-crystalline powder and the low-crystalline powder are shown in FIG. 1.

In the present invention, by using a catalyst made of these calcium phosphates, particularly low-crystalline calcium phosphates singly or as a mixture, wherein the Ca/P mol ratio is adjusted to from 1.4 to 1.8, as it is, or a catalyst by carrying an activation metal or the oxide thereof on the catalyst such that the (ca+metal)/P mol ratio becomes from 1 to 2, the above-described chemical industrial raw materials and a high-octane fuel are efficiently produced.

In this invention, there is no particular restriction on the production method of the calcium phosphate(s) used as the catalyst, and the calcium phosphate(s) can be synthesized by a known synthesizing method such as a dry solid-phase reaction method, a wet precipitation reaction method, a wet solid-phase reaction method, a hydrothermal synthetic method, etc. Also, the low-crystalline calcium phosphate(s) can be obtained by burning the calcium phosphate(s) synthesized by the above-described method in a low-temperature region or by mechanochemically grinding the burned powder. Also, by using a proper template, pores thereof may be controlled. Furthermore, the Ca/P mol ratio can be properly changed at the preparation of the calcium phosphate(s).

For example, in the case of synthesizing hydroxyapatite, a calcium salt solution or phosphate solution of a definite concentration is added dropwise to an aqueous solution with stirring at room temperature while controlling the pH, the product precipitated is collected, washed, dried, ground, and, if necessary, burned to form a catalyst raw material. As the calcium salt used, $Ca(OH)_2$ or $Ca(NO_3)_2$ is preferred and the phosphate used, ammonium phosphate is preferred. The control of the Ca/P mol ratio of hydroxyapatite is carried out by controlling the composition ratio of the salts of the raw materials and the synthetic condition. For example, at the synthesis, when the aqueous solution is controlled to basic with aqueous ammonia, etc., the Ca/P mol ratio is increased, and when the aqueous solution is controlled to neutral or weak acidic with a diluted acid, the Ca/P mol ratio is lowered. Also, hydroxyapatite can be obtained, after mixing calcium phosphates having the known Ca/P mol ratio, by burning the mixture in a moisture atmosphere.

When hydroxyapatite is used as a catalyst, the Ca/P mol ratio is adjusted to from 1.4 to 1.8, and preferably from 1.5 to 1.7 and, if desired, the burning temperature and the burning atmosphere are selected. In this case, it is desirable that the specific area of the catalyst is at least 2 $m^2/g$.

The control of the Ca/P mol ratio in calcium phosphate means to control the kinds and the distribution densities of a solid acid point and a solid base point, which are catalytically active points of the catalyst surface. In this case, the strength and the amounts of the acid point and base point can be determined by $NH_3$-TPD and $CO_3$-TPD, or a pyridine adsorption method, an indicator method, etc.

Also, as a method of controlling the acidity and the basicity of the catalyst surface, it is known to carry a metal as a generally known means.

For example, by carrying a dehydrogenation reaction accelerating metal such as, typically, Ni, Zn, Cu, Pd, or Pt on hydroxyapatite, the effect same as the increase of the Ca/P mol ratio is obtained, that is, the solid basicity is increased.

Also, in the case of hydroxyapatite, by carrying a dehydration reaction accelerating metal such as, typically, Al on the hydroxyapatite, the effect same as lowering the Ca/P mol ratio is obtained, that is, the solid acidic feature is increased.

Accordingly, in place of changing the Ca/P mol ratio, by carrying such a metal on hydroxyapatite, the solid- acid/basicity of the surface of the hydroxyapatite catalyst can be also changed. Also, according to the desired product, it is preferred plural metals are carried on together for obtaining the synergistic effect or improving the durability. Examples of the plural metals which are carried on together include transition metals such as Zn, Co, Cr, Mo, W, Fe, Ni, Cu, Mn, Ti, V, Ga, Zr, Nb, Cd, In, Sn, Sb, Pb, La, Ce, Eu, Y, etc.; noble metals such as Pt, Pd, Rh, Au, Ir, Ru, Ag, etc.; alkali metals or alkaline earth metals such as Ba Na, K, Li, Sr, Ca, Mg, Cs, Rb, etc. Also, as the case may be, the oxides or the sulfides of these metals can be used. These plural metals which are carried on together can be used in the range of from 0.05 to 70 mol % to calcium of the calcium phosphate catalyst and the kinds of them are properly selected according to the purposes.

These metals, metal oxides, or metal sulfides are carried on calcium phosphate by an ordinary method. For example, definite amounts of the salts of the metals which are carried on the calcium phosphate are added to the liquid containing the calcium phosphate(s) obtained by treating as described above, and the mixture is solidified by evaporating off water. Or, the solution of the salts of the metals which are carried on calcium phosphate is sprayed onto the calcium phosphate (s) obtained and after drying, the mixture is burned in the air or in a reducing atmosphere.

Also, a catalyst having both the characteristics of the solid acid point and the solid base point can be synthesized by properly mixing a solid acidic catalyst and a solid basic catalyst.

In the present invention, the synthesis of the chemical industrial raw materials and a high-octane fuel from ethanol as the raw material is practiced by properly selecting the calcium phosphate(s) used, the Ca/P mol ratio, the activation metals, and the reaction conditions (temperature, space velocity, pressure, etc.).

For example, hydroxyapatite the Ca/P mol ratio of which is controlled to 1.6 or lower or calcium tertiary phosphate having an increased specific area value have the property of a solid acid. In this case, By carrying the dehydration reaction accelerating metal such as Al, etc., on the above-described calcium phosphate, the property of the catalyst as a solid acid is increased.

The addition amount of one kind of the metal or the oxide thereof is in the range of from 0.05 to 50 mol % to calcium of the calcium phosphate. When the addition amount is less than 0.05 mol %, the effect of adding the metal is not obtained. When at least 50 mol % one metal component is added, the main constituent becomes the metal phosphate, which holds the position of the calcium phosphate-containing catalyst.

When such a calcium phosphate or metal-carrying calcium phosphate having the increased property as a solid acid is used as the catalyst of the conversion reaction of ethanol, the selectivity of ethylene and diethyl ether in the reaction product can be increased.

For example, in the case of ethylene, the use of the above-described calcium phosphate having replaced with and/or carrying thereon 3 mol % Al improves the catalyst activity as compared with the case of using the above-described calcium phosphate carrying no metal, and the temperature at which 100% the conversion or the selectivity of ethanol is lowered by 50° C. or more.

Also, in the case of diethyl ether, the use of the above-described calcium phosphate carrying Al largely improves the selectively as compared with the case of the above-described calcium phosphate carrying no metal.

Also, by carrying the combination of at least two dehydrogenation reaction accelerating metals such as, Ni, Zn, Cu, Fe, Al, In, Pd, etc., on hydroxyapatite wherein the Ca/P mol ratio is adjusted to at least 1.55 or calcium phosphate having the (Ca+metal)/P mol ratio of from 1 to 2, the property of the catalyst as the solid base is increased. In this case, the addition amounts of the metals are in the range of from 1 to 70 mol % in sum total (the upper limited the addition amount of one metal is 30 mol %) to calcium of the calcium phosphate. When the addition amounts are less than 1 mol %, the above-described catalyst is not excellent as compared with existing known metal-added catalysts. On the other hand, in the case of adding at least 70 mol % the plural metals in sum total, there occurs a problem in the stability of the calcium phosphate.

When such a hydroxyapatite having the strengthened property as the solid base is used for an ethanol conversion reaction as the catalyst, the selectivity of acetaldehyde in the reaction product can be increased.

For example, in the case of using the calcium phosphate carrying thereon Cu, Fe, and Al and having the (Ca+metal)/P mol ratio of from 1 to 2, the conversion and the selectivity of acetaldehyde are largely improved as compared with the case of existing known catalysts.

When a catalyst made of hydroxyapatite the Ca/P mol ratio of which is adjusted to from 1.60 to 1.80, or a catalyst made of calcium phosphate having the (Ca+metal)/P mol ratio of from 1 to 2 and having carried thereon at least one metal selected from the above-described dehydrogenation reaction accelerating metals and dehydration reaction accelerating metals, such as Ba, Na, K, Li, Cs, Sr, Y, Ce, Sb, Eu, Ti, W, and Zr, or the oxides and sulfides of these metals in the range of not more than 50 mol % to calcium of the calcium phosphate such that an acid and a base co-exist is used for the ethanol conversion reaction, the selectivity of 1-butanol can be increased at the range of from 300° C. to 450° C.

For example, hydroxyapatite wherein the Ca/P mol ratio is adjusted to 1.65 or the above-described calcium phosphate carrying thereon Ce can increase the selectivity of 1-butanol to from 60 to 65% at about 400° C.

Also, when a catalyst made of hydroxyapatite wherein the Ca/P mol ratio is adjusted to from 1.55 to 1.80, or a catalyst made of calcium phosphate having the (Ca+metal)/P mol ratio of from 1 to 2 and having carried thereon at least one metal selected from the above-described dehydrogenation reaction accelerating metals and dehydration reaction accelerating metals, such as W, Zr, Al, Zn, Ti, Sb, Y, La, Au, and Na, or the oxides and sulfides of these metals in the range of not more than 50 mol % to calcium of the calcium phosphate such that an acid and a base co-exist is used for the ethanol conversion reaction, the selectivity of 1,3-butadiene can be increased at the range of from 450° C. to 700° C.

For example, hydroxyapatite wherein the Ca/P mol ratio is adjusted to 1.62 or the above-described calcium phosphate carrying thereon Al or Zr can increase the selectivity of 1,3-butadiene to from 35 to 50% at about 500° C.

Furthermore, when a catalyst made of hydroxyapatite wherein the Ca/P mol ratio is adjusted to from 1.55 to 1.80, or a catalyst made of calcium phosphate having the (Ca+metal)/P mol ratio of from 1 to 2 and having carried thereon at least one metal selected from the above-described dehydrogenation reaction accelerating metals and dehydration reaction accelerating metals, such as Ni, Ba, Li, Cs, Zn, Ag, Mn, Ce, Sr, Y, Co, Fe, Sb, Eu, Ti, and W, or the oxides and sulfides of these metals in the range of not more than 50 mol % to calcium of the calcium phosphate such that an acid and a base co-exist is used for the ethanol conversion reaction, the selectivity of a high-octane fuel can be increased at the range of from 300° C. to 700° C.

For example, hydroxyapatite wherein the Ca/P mol ratio is adjusted to 1.65 or the calcium phosphate carrying thereon Li or Zn and having the (Ca+metal)/P mol ratio of from 1 to 2 can increase the selectivity of the high-octane fuel to at least 80% at about from 300° C. to 700° C The high-octane fuel in this invention is a motorcar fuel having at least 96.0 by a Research method octane value test method regulated by JIS K 2280, and mean liquid hydrocarbons containing oxygen-containing compounds such as alcohols, ethers, etc., which are known as octane booster, in the components.

Because the composition of gasoline at present is nonpolar hydrocarbons, when few % water intermixes in gasoline, a trouble occurs in starting of engine, and hence a draining agent is required but the high-octane fuel of the invention contains large amounts of polar oxygen-containing hydrocarbons such as unreacted ethanol, butanol, etc., and is a fuel without need of a draining agent.

Now, the existing amount of the oxygen-containing compounds in the fuel of the invention can be controlled by the Ca/P mol ratio, the addition of the metal, and the reaction temperature. That is, by increasing the Ca/P mole ratio, by adding the dehydrogenation reaction accelerating metal, or by lowering the reaction temperature, the existing amount of the oxygen-containing compounds in the fuel can be increased.

In addition, if necessary, in the case of lowering the content of the oxygen-containing compounds, the Ca/P mol ratio may be lowered, the dehydration reaction accelerating metal is added, or the reaction temperature may be raised.

The calcium phosphate prepared as described above can be used in any form such as, for example, granules, powders, etc., and if necessary, after molding the calcium phosphate to an optional form such as spheres, pellets, a honeycomb form, etc., the molded product is dried and burned at use. The calcium phosphate may be carried on a carrier such as alumina, silica, alumina-silica, zeolite, clay, etc., well-known in persons skilled in the art. Burning is carried out at a temperature of from 200° C. to 1200° C., and preferably from 500° C. to 700° C.

In general, when a solid catalyst is used, it is said that the existence of water in raw materials is not preferred since the activity of the catalyst is lowered. However, in the catalyst of the invention, in the existence of water, lowering of the activity of the catalyst is not observed and thus, the catalyst can be used for a long period of time. Accordingly, in the case of water-containing ethanol, the reaction proceeds sufficiently, and hence the catalyst of the invention has the advantage that crude ethanol which is a simple distillate of fermentation ethanol obtained by a biotechnology can be used in a commercial plant.

The reaction temperature in the invention, at which ethanol is brought into contact with the calcium phosphate catalyst, is usually in the range of from 200° C. to 700° C., and the optimum reaction temperature can be properly selected according to the kind of the catalyst and the kind of the synthesized product. In the reaction with the catalyst of the invention, acetaldehyde, diethyl ether, and 1-butanol are high-selectively obtained in a relatively low-temperature region and ethylene and 1,3-butadiene are high-selectively obtained in a relatively high-temperature region. The gas time space velocity (GHSV) is from 100 to 100,000 (l/h), and preferably from 5,000 to 50,000 (l/h). Also, the space velocity is lower than 100, the economy becomes bad. Also, when the space velocity is higher than 100,000, the temperature control in the inside of the reaction column by endothermic or exothermic becomes difficult to cause a temperature distribution, which results in lowering the selectivity of the desired synthetic product. By contacting ethanol as the vapor-phase directly or under the existence of an inert carrier gas such as nitrogen or helium with the catalyst, the ethanol can be reacted with a good efficiency.

In this case, for keeping the catalyst activity, a reactive gas such as hydrogen, a hydrocarbon, etc., may be adding into the carrier gas. As the reaction system of the reaction column, an any method such as a batch system, a continuous system, a fixed bed system, a moving bed system, or a fluid bed system, may be employed and the reaction may be carried out at normal pressure or under pressure. In the case of a reaction of precipitating a large amount of carbon on the catalyst, a plant by the above-described system incorporating a catalyst regeneration treatment apparatus is desirable. When the catalyst which is used for the synthetic reaction of the above-described chemical industrial raw materials other than the synthetic reaction of ethylene and diethyl ether is used for a long period of time, carbon is precipitated on the surface of the catalyst to lower the ethanol conversion. Therefore, the catalyst is periodically subjected to a regeneration treatment by heating under an oxygen atmosphere, whereby the activity of the catalyst can be regenerated. FIG. 2 is a schematic view of an embodiment of the apparatus of practicing the present invention.

As shown in FIG. 2, ethanol as a raw material is supplied to an alcohol carburetor 2 through a micro-feeder (moderate pressure liquid feed pump) 1. To the alcohol carburetor 2 are supplied a 1% Ar/He-base carrier gas from a gas bomb 3 and a gas from a model gas mixer 4, they enter a reaction pipe 5 together with ethanol, and reaction products according to the reaction temperature are exhausted. The reaction products are chemically confirmed by an analyzer 6.

The reaction products thus obtained can be separated and purified using a separation and purification method which has hitherto been used, such as a rectification, an extraction, an adsorption method, etc.

EXAMPLE

A catalyst was synthesized as follows. Also, for the measurement of the specific area of the powder obtained, SA3100, manufactured by COLTER CO., LTD., was used, and for the measurements of the Ca/P mol ratio and the (Ca+metal)/P mol ratio, a fluorescent X-ray analyzer, RIX1000, manufactured by Rigaku Denki Kogyo K.K. was used.

1) Case of Ethylene Synthesis Catalyst

Preparation of Catalyst

Sample 1

After lightly grinding calcium phosphate having the Ca/P mol ratio of 1.50 by a mortar, the ground product was burned at 700° C. for 2 hours and ground by a mortar to obtained a powder. After dissolving 0.037 g of aluminum nitrate [$Al(NO_3)_3 \cdot 9H_2O$] in 50 ml of distilled water, 10 g of the above-described powder was added to the solution and after stirring the mixture for one day, the mixture was dried at 140° C. The dried product was ground and burned in the air at 700° C. for 2 hours to obtained a powdery catalyst composition containing 0.1 mol % aluminum.

Sample 2

A solution formed by dissolving 232.3 g of calcium nitrate [$Ca(NO_3)_2 \cdot 4H_2O$] in 5.0 liters of distilled water and a solution formed by dissolving 78.87 g of ammonium phosphate [$(NH_4)_2HPO_4$] in 3.0 liters of distilled water were added dropwise to aqueous ammonia having adjusted pH of from 9 to 11 under a nitrogen atmosphere, and the resultant mixture was stirred for one day. Thereafter, the product was collected by filtration, washed with water, and dried at 140° C. to provide a powder having the Ca/P mol ratio of 1.65. After dissolving 0.037 g of aluminum nitrate [$Al(NO_3)_3 \cdot 9H_2O$] in 50 ml of distilled water, 10.0 g of the above-described calcium phosphate powder was added to the solution followed by stirring for one day, the mixture was dried at 140° C., ground, and burned in the air at 700° C. for 2 hours to obtained a powdery catalyst composition containing 0.1 mol % Al to Ca and having the (Ca+Al)/P mol ratio of 1.65

Sample 3

A solution obtained by dissolving 13.65 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 in a nitrogen gas atmosphere followed by stirring for one day. Furthermore, a solution formed by dissolving 0.67 g of aluminum nitrate [$Al(NO_3)_3 \cdot 9H_2O$] in 50 ml of distilled water was added to the above-described mixture and the resultant mixture was stirred for one day. Thereafter, the mixture was evaporated to dryness at 140° C. and after grinding the dried product, the ground product was burned in the air at 700° C. for 2 hours to obtain a powdery catalyst composition containing 3 mol % aluminum to Ca and having the (Ca+Al)/P mol ratio of 1.0.

Sample 4

After lightly grinding calcium phosphate having the Ca/P mol ratio of 1.50 by a mortar, a solution obtained by dissolving 0.67 g of aluminum nitrate [$Al(NO_3)_3 \cdot 9H_2O$] in 50 ml of distilled water was added to the powder and further, the mixture was stirred for one day. Thereafter, the mixture was evaporated to dryness at 140° C., and after grinding, the ground product was burned in the air at 700° C. for 2 hours to obtain a powdery catalyst composition containing 3 mol % aluminum to Ca and having the (Ca+Al)/P mol ratio of 1.50.

Sample 5

A solution obtained by dissolving 22.53 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 in a nitrogen gas atmosphere followed by stirring for one day. Furthermore, a solution obtained by dissolving 0.67 g of aluminum nitrate [$Al(NO_3)_3 \cdot 9H_2O$] in 50 ml of distilled water was added to the above-described mixture, and the resultant mixture was further stirred for one day. Thereafter, the mixture was evaporated to dryness at 140° C., and after grinding, the ground product was burned in the air at 700° C. for 2 hours to obtained a powdery catalyst composition containing 3 mol % aluminum to Ca and having the (Ca+Al)/P mol ratio of 1.65.

Sample 6

A solution obtained by dissolving 27.31 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 in a nitrogen gas atmosphere followed by stirring for one day. Furthermore, a solution obtained by dissolving 0.67 g of aluminum nitrate [$Al(NO_3)_3 \cdot 9H_2O$] in 50 ml of distilled water was added to the above-described mixture, and the resultant mixture was further stirred for one day. Thereafter, the mixture was evaporated to dryness at 140° C., and after grinding, the ground product was burned in the air at 700° C. for 2 hours to obtained a powdery catalyst composition containing 3 mol % aluminum to Ca and having the (Ca+Al)/P mol ratio of 2.00.

Sample 7

By burning a powder synthesized by the same procedure as in the case of preparing Sample 5 in the air at 750° C. for 2 hours, a powdery catalyst composition containing 3 mol % aluminum to Ca and having the (Ca+Al)/P mol ratio of 1.65 was obtained.

Sample 8

A solution obtained by dissolving 11.61 g of calcium nitrate [Ca(NO$_3$) n$_2$.4H$_2$O] in 500 ml of distilled water and a solution obtained by dissolving 7.89 g of ammonium phosphate [(NH$_4$)$_2$HPO$_4$] in 300 ml of distilled water were added dropwise to aqueous ammonia having adjusted pH of from 9 to 11 in a nitrogen gas atmosphere followed by stirring for one day. Furthermore, a solution obtained by dissolving 19.73 g of aluminum nitrate [Al (NO$_3$)$_3$.9H$_2$O] in 500 ml of distilled water was added to the above-described mixture, and the resultant mixture was further stirred for one day. Thereafter, the mixture was evaporated to dryness at 140° C., and after grinding, the ground product was burned in the air at 700° C. for 2 hours to obtained a powdery catalyst composition containing 50 mol % aluminum to Ca and having the (Ca+Al)/P mol ratio of 1.65.

Comparative Sample 1

After lightly grinding calcium phosphate having the Ca/P mol ratio of 1.00 by a mortar, the ground product was burned in the air at 700° C. for 2 hours, and was ground in a mortar to obtain a powder for comparative sample.

Comparative Sample 2

After lightly grinding calcium phosphate having the Ca/P mol ratio of 1.50 by a mortar, the ground product was burned in the air at 700° C. for 2 hours, and was ground in a mortar to obtain a power for comparative sample.

Comparative Sample 3

A solution obtained by dissolving 232.3 g of calcium nitrate [Ca(NO$_3$)$_2$.4H$_2$O] in 5.0 liters of distilled water and a solution obtained by dissolving 78.87 g of ammonium phosphate [(NH$_4$)$_2$HPO$_4$] in 3.0 liters of distilled water were added dropwise to aqueous ammonia having adjusted pH of from 9 to 11 in a nitrogen gas atmosphere followed by stirring for one day. Thereafter, the product was collected by filtration, washed with water, dried at 140° C., and burned in the air at 700° C. for 2 hours to provide a powder for the comparative sample having the Ca/P mol ratio of 1.65.

Comparative Sample 4

After lightly grinding calcium phosphate having the Ca/P mol ratio of 2.00 by a mortar, the ground product was burned in the air at 700° C. for 2 hours and then ground by a mortar to obtained a powder for the comparative sample.

Comparative Sample 5

After dissolving 0.037 g of aluminum nitrate [Al(NO$_3$)$_3$.9H$_2$O] in 50 ml of distilled water, 10 g of the powder of Comparative Sample 3 was added to the solution followed by stirring for one day, the mixture was dried at 140° C., and after drying, was burned in the air at 700° C. for 2 hours to obtained a powder for the comparative sample containing 0.03 mol % aluminum.

Comparative Sample 6

Sample 5 was evaluated at a reaction temperature of 350° C.

Comparative Sample 7

The powder obtained by the synthetic method of Sample 5 was burned in the air at 800° C. for 2 hours to obtain a powder for the comparative sample. The sample was evaluated at a reaction temperature of 750° C.

Comparative Sample 8

Sample 8 was evaluated at a reaction temperature of 350° C.

Comparative Sample 9

The powder obtained by the synthetic method of Sample 8 was burned in the air at 800° C. for 2 hours to obtain a powder for the comparative sample. The sample was evaluated at a reaction temperature of 750° C.

Evaluation of Catalytic Characteristics

Each sample prepared in Samples 1 to 8 and Comparative Samples 1 to 9 was formed to tablets of from #14 to #26. Then 0.6 ml of the tablets were packed in a quartz tube and, a pretreatment, in the case of the sample carrying no metal, a heating (dehydration) treatment was carried out in a carrier gas (1% Ar/He base: flow rate 80 cc/min.), at 500° C. for 30 minutes, and in the case of the metal-carrying sample, a reduction treatment of the metal was carried out in a 20% H$_2$ (He base: flow rate 100 cc/min.) at 500° C. for 30 minutes.

After finishing the pretreatment, the reaction was carried out under the conditions of a ethanol concentration of 20%, a carrier gas flow rate of 80 cc/minute (total flow rate 100 cc/min.) and a space velocity (GHSV) of 10,000 (1/h) at a normal pressure.

In the case of the ethylene synthesis, the reaction temperature was in the range of from 400 to 700° C.

The identification of the reaction gas components was carried out using gas chromatographic mass spectrometer (GC-MS), and the measurements of the conversion of ethanol and the selectivity of the synthesis gas were carried out using a gas chromatograph (GC) (detector: FID) and they were determined by the following formulae from the peak area value of each component.

Ethanol conversion(%)=(1−(peak area value of ethanol after reaction)/(peak area value of ethanol before reaction)×100

Synthesis gas selectivity(%)=(peak area value/(total peak area value−peak area value of remaining ethanol)×100

A space time yield (STY) is defined by the yield (g) of hydrocarbons per 1 liter of catalyst and 1 hour, and by regarding the hydrocarbons as CH$_2$×n, the space time yield was calculated by the following formula.

Space time yield (g/(h×L))=introduced ethanol (mol)×2×14×ethanol conversion × selectivity/catalyst volume As the reaction apparatus, a gas flow-type catalytic reaction apparatus shown in FIG. 2 was used. The evaluation results obtained are shown in Table 1 below.

TABLE 1

EXAMPLES AND COMPARATIVE EXAMPLES OF ETHYLENE SYNTHESIS CATALYSTS

| | Composition | | | Characteristics | | | |
|---|---|---|---|---|---|---|---|
| | (Ca + M)/P | Substituted metal | Substituted amount of metal (mol %) | Specific area (BET) (m²/g) | Reaction temperature (° C.) | Ethanol conversion (%) | Selectivity (%) | Space time yield (STY*) (g/h*L) |

| | (Ca + M)/P | Substituted metal | Substituted amount of metal (mol %) | Specific area (BET) ($m^2/g$) | Reaction temperature (° C.) | Ethanol conversion (%) | Selectivity (%) | Space time yield (STY*) (g/h*L) |
|---|---|---|---|---|---|---|---|---|
| <Example> | | | | | | | | |
| Sample 1 | 1.50 | Al | 0.1 | 2.3 | 500 | 55.8 | 98.1 | 1365 |
| Sample 2 | 1.65 | Al | 0.1 | 37.2 | 500 | 93.6 | 38.3 | 894 |
| Sample 3 | 1.00 | Al | 3 | 10.3 | 500 | 66.2 | 98.6 | 1628 |
| Sample 4 | 1.50 | Al | 3 | 4.7 | 600 | 98.3 | 99.2 | 2432 |
| Sample 5 | 1.65 | Al | 3 | 50.7 | 500 | 97.8 | 92.4 | 2254 |
| Sample 6 | 2.00 | Al | 3 | 6.5 | 500 | 78.6 | 86.4 | 1694 |
| Sample 7 | 1.65 | Al | 3 | 32.9 | 700 | 100.0 | 68.1 | 1699 |
| Sample 8 | 1.65 | Al | 50 | 78.3 | 400 | 96.1 | 53.1 | 1273 |
| <Comparative Example> | | | | | | | | |
| Comparative sample 1 | 1.00 | none | | 5.6 | 500 | 25.8 | 84.6 | 544 |
| Comparative sample 2 | 1.50 | none | | 1.2 | 500 | 18.3 | 97.5 | 445 |
| Comparative sample 3 | 1.65 | none | | 36.4 | 600 | 100.0 | 12.2 | 304 |
| Comparative sample 4 | 2.00 | none | | 7.3 | 500 | 32.4 | 17.4 | 141 |
| Comparative sample 5 | 1.65 | Al | 0.03 | 36.5 | 500 | 88.7 | 13.2 | 292 |
| Comparative sample 6 | 1.65 | Al | 3 | 50.7 | 350 | 35.2 | 10.4 | 91 |
| Comparative sample 7 | 1.65 | Al | 3 | 25.4 | 750 | 100.0 | 6.9 | 172 |
| Comparative sample 8 | 1.65 | Al | 50 | 78.3 | 350 | 73.5 | 12.7 | 233 |
| Comparative sample 9 | 1.65 | Al | 50 | 31.5 | 750 | 100.0 | 3.6 | 90 |

<Reaction condition>: ethanol 20%, SV = 10,000 (1/h), 1 atm, V = 0.6 ml
*Space time yield (STY; $CH_2$ converted) ethanol flow rate (cc/h) × 0.7893/46.07 × 2 × 14 × ethanol conversion × selectivity/catalyst volume 2) Case of Acetaldehyde Synthesis Catalyst Preparation of Catalyst Sample 9

A solution obtained by dissolving 21.88 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 under a nitrogen atmosphere, and the resultant mixture was stirred for one day. Furthermore, a solution obtained by dissolving 0.120 g of copper nitrate [$Cu(NO_3)_2 \cdot 3H_2O$] and 0.201 g of iron (III) nitrate [$Fe(NO_3)_3 \cdot 9H_2O$] in 50 ml of distilled water was added to the solution followed by further stirring for one day. Thereafter, the mixture was evaporated to dryness at 140° C. and after grinding, the ground product was burned in the air at 500° C. for 2 hours to obtain a powdery catalyst composition containing 0.5 mol % each of Cu and Fe to Ca and having the (Ca+Cu+Fe)/P mol ratio of 1.57.

Sample 10

A solution obtained by dissolving 19.71 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 under a nitrogen atmosphere, and the resultant mixture was stirred for one day. Furthermore, solutions obtained by dissolving each of 2.46 g of copper nitrate [$Cu(NO_3)_2 \cdot 3H_2O$] and 4.15 g of iron (III) nitrate [$Fe(NO_3)_3 \cdot 9H_2O$] in 200 ml of distilled water respectively were added to the solution followed by further stirring for one day. Thereafter, the mixture was evaporated to dryness at 140° C. and after grinding, the ground product was burned in the air at 500° C. for 2 hours to obtain a powdery catalyst composition containing 10 mol % each of Cu and Fe to Ca and having the (Ca+Cu+Fe)/P mol ratio of 1.75.

Sample 11

A solution obtained by dissolving 17.68 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 under a nitrogen atmosphere, and the resultant mixture was stirred for one day. Furthermore, solutions obtained by dissolving each of 2.21 g of copper nitrate [$Cu(NO_3)_2 \cdot 3H_2O$] and 3.72 g of iron (III) nitrate [$Fe(NO_3)_3 \cdot 9H_2O$] in 200 ml of distilled water respectively were added to the solution followed by further stirring for one day. Thereafter, the mixture was evaporated to dryness at 140° C. and after grinding, the ground product was burned in the air at 500° C. for 2 hours to obtain a powdery catalyst composition containing 10 mol % each of Cu and Fe to Ca and having the (Ca+Cu+Fe)/P mol ratio of 1.57.

Sample 12

A solution obtained by dissolving 9.72 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 under a nitrogen atmosphere, and the resultant mixture was stirred for one day. Furthermore, solutions obtained by dissolving each of 5.94 g of copper nitrate [$Cu(NO_3)_2 \cdot 3H_2O$] and 10.14 g of iron (III) nitrate [$Fe(NO_3)_3 \cdot 9H_2O$] in 500 ml of distilled water respectively were added to the solution followed by further stirring for one day. Thereafter, the mixture was evaporated to dryness at 140° C. and after grinding, the ground product was burned in the air at 500° C. for 2 hours to obtain a powdery catalyst composition containing 28 mol % each of Cu and Fe to Ca and having the (Ca+Cu+Fe)/P mol ratio of 1.57.

Sample 13

A solution obtained by dissolving 21.88 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 under a nitrogen atmosphere, and the resultant mixture was stirred for one day. Furthermore, solutions obtained by dissolving each of 0.096 g of copper nitrate [$Cu(NO_3)_2 \cdot 3H_2O$], 0.161 g of iron (III) nitrate [$Fe(NO_3)_3 \cdot 9H_2O$], and 0.075 g of aluminum nitrate [$Al(NO_3)_3 \cdot 9H_2O$] in 50 ml of distilled water respectively were added to the solution followed by further stirring for one day. Thereafter, the mixture was evaporated to dryness at 140° C. and after grinding, the ground product was burned in the air at 500° C. for 2 hours to obtain a powdery catalyst composition containing 0.4 mol % Cu, 0.4 mol % Fe, and 0.2 mol % Al to Ca and having the (Ca+Cu+Fe+Al)/P mol ratio of 1.57.

Sample 14

A solution obtained by dissolving 16.57 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 under a nitrogen atmosphere, and the resultant mixture was stirred for one day. Furthermore, solutions obtained by dissolving each of 2.21 g of copper nitrate [$Cu(NO_3)_2 \cdot 3H_2O$], 3.72 g of iron (III) nitrate [$Fe(NO_3)_3 \cdot 9H_2O$], and 1.77 g of aluminum nitrate [$Al(NO_3)_3 \cdot 9H_2O$] in 200 ml of distilled water respectively were added to the solution followed by further stirring for one day. Thereafter, the mixture was evaporated to dryness at 140° C. and after grinding, the ground product was burned in the air at 500° C. for 2 hours to obtain a powdery catalyst composition containing 10 mol % Cu, 10 mol % Fe, and 5 mol % Al to Ca and having the (Ca+Cu+Fe+Al)/P mol ratio of 1.57.

Sample 15

A solution obtained by dissolving 4.22 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 under a nitrogen atmosphere, and the resultant mixture was stirred for one day. Furthermore, solutions obtained by dissolving each of 3.78 g of copper nitrate [$Cu(NO_3)_2 \cdot 3H_2O$], 6.46 g of iron (III) nitrate [$Fe(NO_3)_3 \cdot 9H_2O$], and 3.19 g of aluminum nitrate [$Al(NO_3)_3 \cdot 9H_2O$] in 500 ml of distilled water respectively were added to the solution followed by further stirring for one day. Thereafter, the mixture was evaporated to dryness at 140° C. and after grinding, the ground product was burned in the air at 500° C. for 2 hours to obtain a powdery catalyst composition containing 28 mol % Cu, 28 mol % Fe, and 14 mol % Al to Ca and having the (Ca+Cu+Fe+Al)/P mol ratio of 1.00.

Sample 16

A solution obtained by dissolving 6.63 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 under a nitrogen atmosphere, and the resultant mixture was stirred for one day. Furthermore, solutions obtained by dissolving each of 5.94 g of copper nitrate [$Cu(NO_3)_2 \cdot 3H_2O$], 10.14 g of iron (III) nitrate [$Fe(NO_3)_3 \cdot 9H_2O$], and 5.01 g of aluminum nitrate [$Al(NO_3)_3 \cdot 9H2O$] in 500 ml of distilled water respectively were added to the solution followed by further stirring for one day. Thereafter, the mixture was evaporated to dryness at 140° C. and after grinding, the ground product was burned in the air at 500° C. for 2 hours to obtain a powdery catalyst composition containing 28 mol % Cu, 28 mol % Fe, and 14 mol % Al to Ca and having the (Ca+Cu+Fe+Al)/P mol ratio of 1.57.

Sample 17

A solution obtained by dissolving 6.97 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 under a nitrogen atmosphere, and the resultant mixture was stirred for one day. Furthermore, solutions obtained by dissolving each of 6.24 g of copper nitrate [$Cu(NO_3)_2 \cdot 3H_2O$], 10.66 g of iron (III) nitrate [$Fe(NO_3)_3 \cdot 9H_2O$], and 5.26 g of aluminum nitrate [$Al(NO_3)_3 \cdot 9H_2O$] in 500 ml of distilled water respectively were added to the solution followed by further stirring for one day. Thereafter, the mixture was evaporated to dryness at 140° C. and after grinding, the ground product was burned in the air at 500° C. for 2 hours to obtain a powdery catalyst composition containing 28 mol % Cu, 28 mol % Fe, and 14 mol % Al to Ca and having the (Ca+Cu+Fe+Al)/P mol ratio of 1.65.

Sample 18

A solution obtained by dissolving 8.45 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 under a nitrogen atmosphere, and the resultant mixture was stirred for one day. Furthermore, solutions obtained by dissolving each of 7.57 g of copper nitrate [$Cu(NO_3)_2 \cdot 3H_2O$], 12.92 g of iron (III) nitrate [$Fe(NO_3)_3 \cdot 9H_2O$], and 6.38 g of aluminum nitrate [$Al(NO_3)_3 \cdot 9H_2O$] in 500 ml of distilled water respectively were added to the solution followed by further stirring for one day. Thereafter, the mixture was evaporated to dryness at 140° C. and after grinding, the ground product was burned in the air at 500° C. for 2 hours to obtain a powdery catalyst composition containing 28 mol % Cu, 28 mol % Fe, and 14 mol % Al to Ca and having the (Ca+Cu+Fe+Al)/P mol ratio of 2.00.

Sample 19

Sample 16 was evaluated at a reaction temperature of 300° C.

Sample 20

Sample 16 was evaluated at a reaction temperature of 200° C.

Comparative Sample

Comparative Sample 10

The calcium phosphate of Comparative Sample 1 was treated as in the case of Comparative Sample 1 and burned in the air at 500° C. for 2 hours to obtain a powder for the comparative sample. The sample was evaluated at a reaction temperature of 350° C.

Comparative Sample 11

A solution obtained by dissolving 22.10 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 under a nitrogen atmosphere, and the resultant mixture was stirred for one day. Thereafter, the mixture was evaporated to dryness at 140° C. and after grinding, the ground product was burned in the air at 500° C. for 2 hours to obtain a powdery catalyst composition having the Ca/P mol ratio of 1.57.

Comparative Sample 12

The powder obtained by the synthesis method of Comparative Sample 3 was treated as the case of Comparative Sample 3 and burned in the air at 500° C. for 2 hours to obtained a powder for the comparative sample.

Comparative Sample 13

The powder obtained by the synthesis method of Comparative Sample 4 was treated as the case of Comparative Sample 4 and burned in the air at 500° C. for 2 hours to obtained a powder for the comparative sample.

Comparative Sample 14

A solution obtained by dissolving 22.04 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 under a nitrogen atmosphere, and the resultant mixture was stirred for one day. Furthermore, solutions obtained by dissolving each of 0.023 g of copper nitrate [$Cu(NO_3)_2 \cdot 3H_2O$], 0.038 g of iron (III) nitrate [$Fe(NO_3)_3 \cdot 9H_2O$], and 0.018 g of aluminum nitrate [$Al(NO_3)_3 \cdot 9H_2O$] in 50 ml of distilled water respectively were added to the solution followed by further stirring for one day. Thereafter, the mixture was evaporated to dryness at 140° C. and after grinding, the ground product was burned in the air at 500° C. for 2 hours to obtain a powdery catalyst composition containing 0.1 mol % Cu, 0.1 mol % Fe, and 0.05 mol % Al to Ca and having the (Ca+Cu+Fe+Al)/P mol ratio of 1.57.

Comparative Sample 15

A solution obtained by dissolving 17.68 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 under a nitrogen atmosphere, and the resultant mixture was stirred for one day. Furthermore, a solution obtained by dissolving 4.320 g of copper nitrate [$Cu(NO_3)_2 \cdot 3H_2O$] in 200 ml of a distilled water was added to the above solution and the mixture was further stirred for one day. Thereafter, the mixture was evaporated to dryness at 140° C. and, after grinding, the ground product was burned in the air at 500° C. for 2 hours to obtain a powdery catalyst composition containing 20 mol % Cu to Ca and having the (Ca+Cu)/P mol ratio of 1.57.

Comparative Sample 16

Sample 16 was evaluated at a reaction temperature of 150° C.

Comparative Sample 17

Sample 16 was evaluated at a reaction temperature of 500° C.

Comparative Sample 18

MgO (reagent) which was a typical solid base was used.

Evaluation of Catalytic Characteristics

Each sample prepared in Samples 9 to 20 and Comparative Samples 10 to 18 was formed to tablets of from #14 to #26. Then, the pretreatment as the case of ethylene was applied to the sample. After finishing the pretreatment, the reaction was carried out under the conditions of a ethanol concentration of 20%, a carrier gas flow rate of 80 cc/minute (total flow rate 100 cc/min.) and a space velocity (GHSV) of 10,000 (l/h) at a normal pressure.

In the case of the synthesis of acetaldehyde, the reaction was carried out at a reaction temperature of the range of from 200 to 450° C. The identification and the determination of the reaction gas were carried out as in the case of ethylene. As the reaction apparatus, a gas flow-type catalytic reaction apparatus shown in FIG. 2 was used.

The evaluation results are shown in Table 2 below.

TABLE 2

EXAMPLES AND COMPARATIVE EXAMPLES OF ACETALDEHYDE SYNTHESIS CATALYSTS

| | Composition | | | Characteristics | | | |
|---|---|---|---|---|---|---|---|
| | (Ca + M)/P | Substituted metal | Substituted amount of metal (mol %) | Specific area (BET) (m²/g) | Reaction temperature (° C.) | Ethanol conversion (%) | Selectivity (%) | Space time yield (STY*) (g/h*L) |

| | (Ca + M)/P | Substituted metal | Substituted amount of metal (mol %) | Specific area (BET) (m²/g) | Reaction temperature (° C.) | Ethanol conversion (%) | Selectivity (%) | Space time yield (STY*) (g/h*L) |
|---|---|---|---|---|---|---|---|---|
| <Example> | | | | | | | | |
| Sample 9 | 1.57 | Cu, Fe | 0.5, 0.5 | 29.3 | 450 | 45.2 | 52.6 | 593 |
| Sample 10 | 1.75 | Cu, Fe | 10, 10 | 3.1 | 450 | 56.8 | 55.8 | 791 |
| Sample 11 | 1.57 | Cu, Fe | 10, 10 | 32.2 | 400 | 68.7 | 66.6 | 1141 |
| Sample 12 | 1.57 | Cu, Fe | 28, 28 | 46.1 | 350 | 73.1 | 76.8 | 1400 |
| Sample 13 | 1.57 | Cu, Fe, Al | 0.4, 0.4, 0.2 | 30.7 | 350 | 24.2 | 62.9 | 380 |
| Sample 14 | 1.57 | Cu, Fe, Al | 10, 10, 5 | 35.8 | 350 | 82.6 | 74.7 | 1539 |
| Sample 15 | 1.00 | Cu, Fe, Al | 28, 28, 14 | 10.3 | 350 | 48.3 | 63.4 | 764 |
| Sample 16 | 1.57 | Cu, Fe, Al | 28, 28, 14 | 78.6 | 350 | 96.5 | 84.3 | 2029 |
| Sample 17 | 1.65 | Cu, Fe, Al | 28, 28, 14 | 83.4 | 350 | 86.8. | 85.2 | 1845 |
| Sample 18 | 2.00 | Cu, Fe, Al | 28, 28, 14 | 16.7 | 400 | 88.1 | 76.3 | 1677 |
| Sample 19 | 1.57 | Cu, Fe, Al | 28, 28, 14 | 78.6 | 300 | 76.9 | 78.6 | 1508 |
| Sample 20 | 1.57 | Cu, Fe, Al | 28, 28, 14 | 78.6 | 200 | 37.6 | 63.1 | 592 |
| <Comparative Example> | | | | | | | | |
| Comparative sample 10 | 1.00 | none | | 7.5 | 350 | 3.3 | 0.0 | 0 |
| Comparative sample 11 | 1.57 | none | | 37.6 | 350 | 12.4 | 0.6 | 2 |
| Comparative sample 12 | 1.65 | none | | 43.2 | 400 | 38.1 | 5.9 | 56 |
| Comparative sample 13 | 2.00 | none | | 8.8 | 350 | 4.1 | 15.8 | 16 |
| Comparative sample 14 | 1.57 | Cu, Fe, Al | 0.1, 0.1, 0.05 | 30.7 | 350 | 17.3 | 26.9 | 116 |
| Comparative sample 15 | 1.57 | Cu | 20 | 4.7 | 350 | 13.9 | 63.1 | 219 |
| Comparative sample 16 | 1.57 | Cu, Fe, Al | 28, 28, 14 | 78.6 | 150 | 3.6 | 42.6 | 38 |
| Comparative sample 17 | 1.57 | Cu, Fe, Al | 28, 28, 14 | 78.6 | 500 | 98.4 | 6.5 | 160 |
| Comparative sample 18 | | | | 5.5 | 400 | 2.2 | 53.8 | 30 |

<Reaction condition>: ethanol 20%, SV = 10,000 (1/h), 1 atm, V = 0.6 ml
*Space time yield (STY; $CH_2$ converted) ethanol flow rate (cc/h) × 0.7893/46.07 × 2 × 14 × ethanol conversion × selectivity/catalyst volume 3) Case of Diethyl Ether Synthesis Catalyst Preparation of Catalyst Sample 21

After lightly grinding calcium phosphate having the Ca/P mol ratio of 1.45 by a mortar, the ground product was burned at 700° C. for 2 hours and ground by a mortar to obtained a powder. After dissolving 0.037 g of aluminum nitrate [Al(NO$_3$)$_3$.9H$_2$O] in 50 ml of distilled water, 10 g of the above-described powder was added to the solution, after stirring the mixture for one day, the mixture was dried at 140° C. and the dried product was ground and burned in the air at 700° C. for 2 hours to obtained a powdery catalyst composition containing 0.1 mol % aluminum.

Sample 22

After dissolving 0.037 g of aluminum nitrate [Al(NO$_3$)$_3$.9H$_2$O] in 50 ml of distilled water, 10 g of the powder obtained in the synthesis method of Comparative Example 11 was added to the solution followed by stirring for one day, the mixture was dried at 140° C. and after grinding, was burned in the air at 700° C. for 2 hours to obtain a powdery catalyst composition containing 0.1 mol % aluminum.

Sample 23

Sample 22 was evaluated at a reaction temperature of 400° C.

Sample 24

By lightly grinding calcium phosphate having the Ca/P mol ratio of 1.00 by a mortor, a powder was obtained. After dissolving 1.24 g of aluminum nitrate [Al(NO$_3$)$_3$.9H$_2$O] in 200 ml of distilled water, 10 g of the above-described powder was added to the solution followed by stirring for one day, the mixture was dried at 140° C., and after grinding, was burned in the air at 700° C. for 2 hours to obtain a powdery catalyst composition containing 5 mol % Al to Ca and having the (Ca+Al)/P mol ratio of about 1.0.

Sample 25

A solution obtained by dissolving 20.99 g of calcium nitrate [Ca(NO$_3$)$_2$.4H$_2$O] in 500 ml of distilled water and a solution obtained by dissolving 7.89 g of ammonium phosphate [(NH$_4$)$_2$HPO$_4$] in 300 ml of distilled water were added dropwise to aqueous ammonia having adjusted pH of from 9 to 11 under a nitrogen atmosphere, and the resultant mixture was stirred for one day. Furthermore, a solution obtained by dissolving 1.77 g of aluminum nitrate [Al(NO$_3$)$_3$.9H$_2$O] in 200 ml of distilled water was added to the above solution followed by further stirring for one day. Thereafter, the mixture was evaporated to dryness at 140° C. and, after grinding, the ground product was burned in the air at 700° C. for 2 hours to obtain a powdery catalyst composition containing 5 mol % Al to Ca and having the (Ca+Al)/P mol ratio of 1.57.

Sample 26

A solution obtained by dissolving 22.06 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 under a nitrogen atmosphere, and the resultant mixture was stirred for one day. Furthermore, a solution obtained by dissolving 1.86 g of aluminum nitrate [$Al(NO_3)_3 \cdot 9H_2O$] in 200 ml of distilled water was added to the above-described solution followed by further stirring for one day. Thereafter, the mixture was evaporated to dryness at 140° C. and, after grinding, the ground product was burned in the air at 700° C. for 2 hours to obtain a powdery catalyst composition containing 5 mol % Al to Ca and having the (Ca+Al)/P mol ratio of 1.65.

Sample 27

By lightly grinding calcium phosphate having the Ca/P mol ratio of 2.00 by a motor, a powder was obtained. After dissolving 2.48 g of aluminum nitrate [$Al(NO_3)_3 \cdot 9H_2O$] in 200 ml of distilled water, 10 g of the above-described powder was added to the solution followed by stirring for one day, the mixture was dried at 140° C., and after grinding, was burned in the air at 700° C. for 2 hours to obtain a powdery catalyst composition containing 5 mol % Al to Ca and having the (Ca+Al)/P mol ratio of about 2.0.

Sample 28

A solution obtained by dissolving 11.05 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 under a nitrogen atmosphere, and the resultant mixture was stirred for one day. Furthermore, a solution obtained by dissolving 18.78 g of aluminum nitrate [$Al(NO_3)_3 \cdot 9H_2O$] in 500 ml of distilled water was added to the above-described solution followed by further stirring for one day. Thereafter, the mixture was evaporated to dryness at 140° C. and, after grinding, the ground product was burned in the air at 700° C. for 2 hours to obtain a powdery catalyst composition containing 50 mol % Al to Ca and having the (Ca+Al)/P mol ratio of 1.57.

Sample 29

Sample 28 was evaluated at a reaction temperature of 350° C.

Sample 30

Sample 28 was evaluated at a reaction temperature of 300° C.

Sample 31

Sample 28 was evaluated at a reaction temperature of 200° C.

Comparative Sample 19

Comparative Sample 1 was used.

Comparative Sample 20

The calcium phosphate of Comparative Sample 11 was treated as in Comparative Sample 11 and burned in the air at 700° C. for 2 hours to obtained a powder for the comparative sample.

Comparative Sample 21

Comparative Sample 3 was used.

Comparative Sample 22

Comparative Sample 4 was used.

Comparative Sample 23

After dissolving 0.011 g of aluminum nitrate [$Al(NO_3)_3 \cdot 9H_2O$] in 50 ml of distilled water, 10 g of the powder obtained by the synthesis method of Comparative Sample 11 was added to the solution followed by stirring for one day, the mixture was dried at 140° C. and after grinding, was burned in the air at 700° C. for 2 hours to obtain a powdery catalyst composition containing 0.03 mol % aluminum.

Comparative Sample 24

Sample 25 was evaluated at a reaction temperature of 200° C.

Comparative Sample 25

Sample 25 was evaluated at a reaction temperature of 450° C.

Comparative Sample 26

Sample 28 was evaluated at a reaction temperature of 150° C.

Comparative Sample 27

Sample 28 was evaluated at a reaction temperature of 450° C.

Evaluation of Catalytic Characteristics

Each sample prepared in Samples 21 to 31 and Comparative Samples 19 to 27 was formed to tablets of from #14 to #26. Then, the pretreatment was applied to the sample as the case of ethylene.

After finishing the pretreatment, the reaction was carried out under the conditions of a ethanol concentration of 20%, a carrier gas flow rate of 80 cc/minute (total flow rate 100 cc/min.) and a space velocity (GHSV) of 10,000 (l/h) at a normal pressure. In the case of the synthesis of diethyl ether, the synthesis was carried out at a reaction temperature of from 200° C. to 400° C. The identification and the determination of the reaction gas were carried out by the same methods as the case of ethylene. As the reaction apparatus, the gas flow-type catalytic reaction apparatus shown in FIG. 2 was used.

The evaluation results are shown in Table 3 below.

TABLE 3

EXAMPLES AND COMPARATIVE EXAMPLES OF DIETHYL ETHER SYNTHESIS CATALYSTS

| | Composition | | | Characteristics | | | |
|---|---|---|---|---|---|---|---|
| | (Ca + M)/P | Substituted metal | Substituted amount of metal (mol %) | Specific area (BET) (m²/g) | Reaction temperature (° C.) | Ethanol conversion (%) | Selectivity (%) | Space time yield (STY*) (g/h*L) |

| | (Ca + M)/P | Substituted metal | Substituted amount of metal (mol %) | Specific area (BET) (m²/g) | Reaction temperature (° C.) | Ethanol conversion (%) | Selectivity (%) | Space time yield (STY*) (g/h*L) |
|---|---|---|---|---|---|---|---|---|
| <Example> | | | | | | | | |
| Sample 21 | 1.45 | Al | 0.1 | 2.8 | 400 | 35.9 | 59.2 | 530 |
| Sample 22 | 1.57 | Al | 0.1 | 29.2 | 350 | 27.4 | 87.4 | 597 |
| Sample 23 | 1.57 | Al | 0.1 | 29.2 | 400 | 55.7 | 55.8 | 775 |
| Sample 24 | 1.00 | Al | 5 | 4.3 | 350 | 26.9 | 93.2 | 625 |
| Sample 25 | 1.57 | Al | 5 | 58.9 | 350 | 52.3 | 94.2 | 1229 |
| Sample 26 | 1.65 | Al | 5 | 52.3 | 250 | 22.2 | 91.2 | 505 |
| Sample 27 | 2.00 | Al | 5 | 7.2 | 350 | 29.6 | 82.4 | 608 |
| Sample 28 | 1.57 | Al | 50 | 76.3 | 400 | 97.3 | 43.1 | 1046 |
| Sample 29 | 1.57 | Al | 50 | 76.3 | 350 | 82.3 | 86.3 | 1772 |
| Sample 30 | 1.57 | Al | 50 | 76.3 | 300 | 52.8 | 94.1 | 1239 |
| Sample 31 | 1.57 | Al | 50 | 76.3 | 200 | 24.6 | 96.4 | 592 |
| <Comparative Example> | | | | | | | | |
| Comparative sample 19 | 1.00 | none | | 5.6 | 350 | 1.8 | 20.5 | 9 |
| Comparative sample 20 | 1.57 | none | | 27.4 | 300 | 4.2 | 25.5 | 27 |
| Comparative sample 21 | 1.65 | none | | 36.4 | 250 | 1.6 | 0.3 | 0 |
| Comparative sample 22 | 2.00 | none | | 7.3 | 350 | 2.2 | 0.0 | 0 |
| Comparative sample 23 | 1.57 | Al | 0.03 | 27.8 | 350 | 11.2 | 31.5 | 88 |
| Comparative sample 24 | 1.57 | Al | 5 | 58.9 | 200 | 1.4 | 96.2 | 34 |
| Comparative sample 25 | 1.57 | Al | 5 | 58.9 | 450 | 78.6 | 2.2 | 43 |
| Comparative sample 26 | 1.57 | Al | 50 | 76.3 | 150 | 3.6 | 96.8 | 87 |
| Comparative sample 27 | 1.57 | Al | 50 | 76.3 | 450 | 99.8 | 1.2 | 30 |

<Reaction condition>: ethanol 20%, SV = 10,000 (1/h), 1 atm, V = 0.6 ml
*Space time yield (STY; $CH_2$ converted) ethanol flow rate (cc/h) × 0.7893/46.07 × 2 × 14 × ethanol conversion × selectivity/catalyst volume

4) Case of 1-butanol Synthesis Catalyst

Preparation of Catalyst

Sample 32

A solution obtained by dissolving 225.2 g of calcium nitrate $[Ca(NO_3)_2.4H_2O]$ in 5.0 liters of distilled water and a solution obtained by dissolving 78.87 g of ammonium phosphate $[(NH_4)_2HPO_4]$ in 3.0 liters of distilled water were added dropwise to aqueous ammonia having adjusted pH of from 9 to 11 under a nitrogen atmosphere, and the mixture was stirred for one day. Thereafter, the product was collected by filtration, washed with water, and after drying at 140° C., burned in the air at 700° C. for 2 hours to obtain a powdery catalyst composition having the Ca/P mol ratio of 1.60.

Sample 33

Comparative sample 3 was used.

Sample 34

Comparative Sample 3 was evaluated at a reaction temperature of 400° C.

Sample 35

Comparative Sample 3 was evaluated at a reaction temperature of 350° C.

Sample 36

A solution obtained by dissolving 239.3 g of calcium nitrate $[Ca(NO_3)_2.4H_2O]$ in 5.0 liters of distilled water and a solution obtained by dissolving 78.87 g of ammonium phosphate $[(NH_4)_2HPO_4]$ in 3.0 liters of distilled water were added dropwise to aqueous ammonia having adjusted pH of from 9 to 11 under a nitrogen atmosphere, and the mixture was stirred for one day. Thereafter, the product was collected by filtration, washed with water, and after drying at 140° C., burned in the air at 900° C. for 2 hours to obtain a powdery catalyst composition having the Ca/P mol ratio of 1.7 0.

Sample 37

A solution obtained by dissolving 253.4 g of calcium nitrate $[Ca(NO_3)_2.4H_2O]$ in 5.0 liters of distilled water and a solution obtained by dissolving 78.87 g of ammonium phosphate $[(NH_4)_2HPO_4]$ in 3.0 liters of distilled water were added dropwise to aqueous ammonia having adjusted pH of from 9 to 11 under a nitrogen atmosphere, and the mixture was stirred for one day. Thereafter, the product was collected by filtration, washed with water, and after drying at 140° C., burned in the air at 700° C. for 2 hours to obtain a powdery catalyst composition having the Ca/P mol ratio of 1.8 0.

Sample 38

After dissolving 1.24 g of cerium nitrate $[Ce(NO_3)_3.6H_2O]$ in 200 ml of distilled water, 9.59 g of the powder obtained by the synthetic method of Comparative Sample 3 was added to the solution followed by stirring for one day. Then, the product was dried at 140° C. and after grinding, was burned in the air at 700° C. for 2 hours to obtain a powdery catalyst composition containing 3 mol % Ce to Ca and having the (Ca+Ce)/P mol ratio of 1.65.

Sample 39

Sample 38 was evaluated at a reaction temperature of 400° C.

Sample 40

Sample 38 was evaluated at a reaction temperature of 350° C.

Sample 41

Sample 38 was evaluated at a reaction temperature of 300° C.

Sample 42

A solution obtained by dissolving 7.04 g of calcium nitrate $[Ca(NO_3)_2 \cdot 4H_2O]$ in 500 ml of distilled water and a solution obtained by dissolving 7.89 g of ammonium phosphate $[(NH_4)_2HPO_4]$ in 300 ml of distilled water were added dropwise to aqueous ammonia having adjusted pH of from 9 to 11 under a nitrogen atmosphere, and the mixture was stirred for one day. Furthermore, a solution obtained by dissolving 8.29 g of magnesium nitrate $[Mg(NO_3)_2 \cdot 6H_2O]$ in 500 ml of distilled water was added to the above-described solution followed by further stirring for one day. Thereafter, the mixture was evaporated to dryness at 140° C. and after grinding the dried product, the ground product was burned in the air at 700° C. for 2 hours to obtain a powdery catalyst composition containing 50 mol % Mg to Ca and having the (Ca+Mg)/P mol ratio of 1.00.

Sample 43

A solution obtained by dissolving 14.78 g of calcium nitrate $[Ca(NO_3)_2 \cdot 4H_2O]$ in 500 ml of distilled water and a solution obtained by dissolving 7.89 g of ammonium phosphate $[(NH_4)_2HPO_4]$ in 300 ml of distilled water were added dropwise to aqueous ammonia having adjusted pH of from 9 to 11 under a nitrogen atmosphere, and the mixture was stirred for one day. Furthermore, a solution obtained by dissolving 7.22 g of magnesium nitrate $[Mg(NO_3)_2 \cdot 6H_2O]$ in 500 ml of distilled water was added to the above-described solution followed by further stirring for one day. Thereafter, the mixture was evaporated to dryness at 140° C. and after grinding, the ground product was burned in the air at 700° C. for 2 hours to obtain a powdery catalyst composition containing 30 mol % Mg to Ca and having the (Ca+Mg)/P mol ratio of 1.50.

Sample 44

A solution obtained by dissolving 11.61 g of calcium nitrate $[Ca(NO_3)_2 \cdot 4H_2O]$ in 500 ml of distilled water and a solution obtained by dissolving 7.89 g of ammonium phosphate $[(NH_4)_2HPO_4]$ in 300 ml of distilled water were added dropwise to aqueous ammonia having adjusted pH of from 9 to 11 under a nitrogen atmosphere, and the mixture was stirred for one day. Furthermore, a solution obtained by dissolving 14.26 g of cerium nitrate $[Ce(NO_3)_3 \cdot 6H_2O]$ in 500 ml of distilled water was added to the above solution followed by further stirring for one day. Thereafter, the mixture was evaporated to dryness at 140° C. and after grinding, the ground product was burned in the air at 700° C. for 2 hours to obtain a powdery catalyst composition containing 50 mol % Ce to Ca and having the (Ca+Ce)/P mol ratio of 1.65.

Sample 45

A solution obtained by dissolving 14.08 g of calcium nitrate $[Ca(NO_3)_2 \cdot 4H_2O]$ in 500 ml of distilled water and a solution obtained by dissolving 7.89 g of ammonium phosphate $[(NH_4)_2HPO_4]$ in 300 ml of distilled water were added dropwise to aqueous ammonia having adjusted pH of from 9 to 11 under a nitrogen atmosphere, and the mixture was stirred for one day. Furthermore, solutions obtained by dissolving each of 11.96 g of cerium nitrate $[Ce(NO_3)_3 \cdot 6H_2O]$ and 9.18 g of aluminum nitrate $[Al(NO_3)_3 \cdot 9H_2O]$ in 500 ml of distilled water respectively were added to the above solution followed by further stirring for one day. Thereafter, the mixture was evaporated to dryness at 140° C. and after grinding, the ground product was burned in the air at 700° C. for 2 hours to obtain a powdery catalyst composition containing 30 mol % Ce and 20 mol % Al to Ca and having the (Ca+CE+Al)/P mol ratio of 2.00.

Comparative Sample 28

Comparative Sample 1 was used.

Comparative Sample 29

A solution obtained by dissolving 211.1 g of calcium nitrate $[Ca(NO)_2 \cdot 4H_2O]$ in 5.0 liters of distilled water and a solution obtained by dissolving 78.87 g of ammoniumphosphate $[(NH_4)_2HPO_4]$ in 3.0 liters of distilled water were added dropwise to aqueous ammonia having adjusted pH of from 9 to 11 under a nitrogen atmosphere, and the mixture was stirred for one day. Thereafter, the product was collected by filtration, washed with water, and after drying at 140° C., burned in the air at 700° C. for 2 hours to obtain a powdery catalyst composition having the Ca/P mol ratio of 1.50.

Comparative Sample 30

The calcium phosphate of Comparative Sample 3 was treated as the case of Comparative Sample 3 and burned in the air at 1200° C. for 2 hours to obtain a powder for the comparative sample.

Comparative Sample 31

Comparative Sample 4 was used.

Comparative Sample 32

Comparative Sample 3 was evaluated at a reaction temperature of 250° C.

Comparative Sample 33

Comparative Sample 3 was evaluated at a reaction temperature of 500° C.

Comparative Sample 34

Sample 38 was evaluated at a reaction temperature of 250° C.

Comparative Sample 35

Sample 38 was evaluated at a reaction temperature of 500° C.

Evaluation of Catalytic Characteristics

Each sample prepared in Samples 32 to 45 and Comparative Samples 28 to 35 was formed to tablets of from #14 to #26. Then, the pretreatment was applied to the sample as the case of ethylene.

After finishing the pretreatment, the reaction was carried out under the conditions of a ethanol concentration of 20%, a carrier gas flow rate of 80 cc/minute (total flow rate 100 cc/min.) and a space velocity (GHSV) of 10,000 (1/h) at a normal pressure. In the case of the synthesis of 1-butanol, the synthesis was carried out at a reaction temperature of from 300° C. to 450° C. The identification and the determination of the reaction gas were carried out by the same methods as the case of ethylene. As the reaction apparatus, the gas flow-type catalytic reaction apparatus shown in FIG. 2 was used.

The evaluation results are shown in Table 4 below.

Sample 47

The calcium phosphate of Sample 32 was treated as the case of Sample 32 and burned in the air at 1000° C. for 2 hours to obtain a powdery catalyst composition.

Sample 48

A solution obtained by dissolving 228.0 g of calcium nitrate $[Ca(NO_3)_2 \cdot 4H_2O]$ in 5.0 liters of distilled water and a solution obtained by dissolving 78.87 g of ammonium phosphate $[(NH_4)_2HPO_4]$ in 3.0 liters of distilled water were added dropwise to aqueous ammonia having adjusted pH of from 9 to 11 under a nitrogen atmosphere, and the mixture was stirred for one day. Thereafter, the product was collected by filtration, washed with water, and after drying at 140° C., burned in the air at 700° C. for 2 hours to obtain a powdery catalyst composition having the Ca/P mol ratio of 1.62.

TABLE 4

EXAMPLES AND COMPARATIVE EXAMPLES OF 1-BUTANOL SYNTHESIS CATALYSTS

| | Composition | | | Characteristics | | | |
|---|---|---|---|---|---|---|---|
| | (Ca + M)/P | Substituted metal | Substituted amount of metal (mol %) | Specific area (BET) (m²/g) | Reaction temperature (° C.) | Ethanol conversion (%) | Selectivity (%) | Space time yield (STY*) (g/h*L) |

| | (Ca + M)/P | Substituted metal | Substituted amount of metal (mol %) | Specific area (BET) (m²/g) | Reaction temperature (° C.) | Ethanol conversion (%) | Selectivity (%) | Space time yield (STY*) (g/h*L) |
|---|---|---|---|---|---|---|---|---|
| <Example> | | | | | | | | |
| Sample 32 | 1.60 | none | | 26.7 | 400 | 23.4 | 48.6 | 284 |
| Sample 33 | 1.65 | none | | 36.4 | 450 | 57.9 | 37.5 | 542 |
| Sample 34 | 1.65 | none | | 36.4 | 400 | 32.1 | 65.3 | 523 |
| Sample 35 | 1.65 | none | | 36.4 | 350 | 18.6 | 61.8 | 287 |
| Sample 36 | 1.70 | none | | 2.2 | 450 | 21.5 | 48.1 | 258 |
| Sample 37 | 1.80 | none | | 35.2 | 400 | 22.6 | 36.1 | 204 |
| Sample 38 | 1.65 | Ce | 3 | 50.4 | 450 | 64.2 | 41.2 | 660 |
| Sample 39 | 1.65 | Ce | 3 | 50.4 | 400 | 42.3 | 63.7 | 672 |
| Sample 40 | 1.65 | Ce | 3 | 50.4 | 350 | 28.4 | 62.1 | 440 |
| Sample 41 | 1.65 | Ce | 3 | 50.4 | 300 | 12.1 | 53.2 | 161 |
| Sample 42 | 1.00 | Mg | 50 | 6.7 | 450 | 46.5 | 28.6 | 332 |
| Sample 43 | 1.50 | Mg | 30 | 73.1 | 400 | 43.2 | 32.5 | 350 |
| Sample 44 | 1.65 | Ce | 50 | 82.1 | 400 | 47.1 | 55.6 | 653 |
| Sample 45 | 2.00 | Ce, Al | 30, 20 | 18.6 | 450 | 56.8 | 26.4 | 374 |
| <Comparative Example> | | | | | | | | |
| Comparative sample 28 | 1.00 | none | | 5.6 | 400 | 3.2 | 0.0 | 0 |
| Comparative sample 29 | 1.50 | none | | 42.3 | 350 | 18.6 | 0.0 | 0 |
| Comparative sample 30 | 1.65 | none | | 0.8 | 450 | 7.3 | 40.2 | 73 |
| Comparative sample 31 | 2.00 | none | | 7.3 | 400 | 7.4 | 23.5 | 43 |
| Comparative sample 32 | 1.65 | none | | 36.4 | 250 | 1.4 | 26.9 | 9 |
| Comparative sample 33 | 1.65 | none | | 36.4 | 500 | 91.9 | 4.4 | 101 |
| Comparative sample 34 | 1.65 | Ce | 3 | 50.4 | 250 | 2.3 | 28.6 | 16 |
| Comparative sample 35 | 1.65 | Ce | 3 | 50.4 | 500 | 93.1 | 3.6 | 84 |

<Reaction condition>: ethanol 20%, SV = 10,000 (1/h), 1 atm, V = 0.6 ml
*Space time yield (STY; $CH_2$ converted) ethanol flow rate (cc/h) × 0.7893/46.07 × 2 × 14 × ethanol conversion × selectivity/catalyst volume

5) Case of 1,3-butadiene Synthesis Catalyst

Preparation of Catalyst

Sample 46

Comparative Sample 20 was used.

Sample 49

Sample 48 was evaluated at a reaction temperature of 550° C.

Sample 50

Sample 48 was evaluated at a reaction temperature of 500° C.

Sample 51

Sample 48 was evaluated at a reaction temperature of 450° C.

Sample 52

Comparative Sample 3 was used.

Sample 53

The calcium phosphate of Sample 36 was treated as the case of Sample 36 and then burned in the air at 700° C. for 2 hours to obtain a powdery catalyst composition.

Sample 54

Sample 37 was used.

Sample 55

A solution obtained by dissolving 225.7 g of calcium nitrate $[Ca(NO_3)_2 \cdot 4H_2O]$ in 5.0 liters of distilled water and a solution obtained by dissolving 78.87 g of ammonium phosphate $[(NH_4)_2HPO_4]$ in 3.0 liters of distilled water were added dropwise to aqueous ammonia having adjusted pH of from 9 to 11 under a nitrogen atmosphere, and the mixture was stirred for one day. Thereafter, the product was collected by filtration, washed with water, and dried at 140° C. to obtain a powder. After dissolving 0.224 g of zirconium (IV) chloride $(ZrCl_4)$ in 100 ml of distilled water, 9.91 g of the above-described powder was added to the solution followed by stirring for one day, the mixture was dried at 140° C., and after grinding, was burned in the air at 700° C. for 2 hours to obtain a powdery catalyst composition containing 1 mol % Zr to Ca and having the (Ca+Zr)/P mol ratio of 1.62.

Sample 56

Sample 55 was evaluated at a reaction temperature of 450° C.

Sample 57

Sample 2 was used.

Sample 58

Sample 2 was evaluated at a reaction temperature of 500° C.

Sample 59

Sample 2 was evaluated at a reaction temperature of 450° C.

Sample 60

A solution obtained by dissolving 225.3 g of calcium nitrate $[Ca(NO_3)_2 \cdot 4H_2]$ in 5.0 liters of distilled water and a solution obtained by dissolving 78.87 g of ammonium phosphate $[(NH_4)_2HPO_4]$ in 3.0 liters of distilled water were added dropwise to aqueous ammonia having adjusted pH of from 9 to 11 under a nitrogen atmosphere, and the mixture was stirred for one day. Thereafter, the product was collected by filtration, washed with water, and dried at 140° C. to obtain a powder. After dissolving 0.847 g of titanium tetraisopropoxide $\{[(CH_3)_2CHO]_4Ti\}$ in 100 ml of ethanol, 9.86 g of the above-described powder was added to the solution followed by stirring for one day. The mixture was dried at 140° C., and after grinding, was burned in the air at 700° C. for 2 hours to obtain a powdery catalyst composition containing 3 mol % Ti to Ca and having the (Ca+Ti)/P mol ratio of 1.65

Sample 61

After dissolving 0.715 g of tungstic acid $(H_2WO_4)$ in 100 ml of distilled water, 9.47 g of the calcium phosphate synthesized by Sample 60 was added to the solution followed by stirring for one day. Then, the mixture was dried at 140° C., and after grinding, was burned in the air at 700° C. for 2 hours to obtain a powdery catalyst composition containing 3 mol % W to Ca and having the (Ca+W)/P mol ratio of 1.65.

Sample 62

After dissolving 0.685 g of zirconium (IV) chloride $(ZrCl_4)$ in 100 ml of distilled water, 9.73 g of the calcium phosphate synthesized by Sample 60 was added to the solution followed by stirring for one day. Then, the mixture was dried at 140° C., and after grinding, was burned in the air at 700° C. for 2 hours to obtained a powdery catalyst composition containing 3 mol % Zr to Ca and having the (Ca+Zr)/P mol ratio of 1.65.

Sample 63

Sample 42 was used.

Sample 64

Sample 43 was used.

Sample 65

A solution obtained by dissolving 11.61 g of calcium nitrate $[Ca(NO_3)_2 \cdot 4H2O]$ in 500 ml of distilled water and a solution obtained by dissolving 7.89 g of ammonium phosphate $[(NH4)_2HPO_4]$ in 300 ml of distilled water were added dropwise to aqueous ammonia having adjusted pH of from 9 to 11 under a nitrogen atmosphere, and the mixture was stirred for one day. Furthermore, a solution obtained by dissolving 9.13 g of zirconium (IV) chloride $(ZrCl_4)$ in 500 ml of distilled water was added to the above-described mixture followed by further stirring for one day. Thereafter, the mixture was evaporated to dryness at 140° C. and after grinding, the ground product was burned in the air at 700° C. for 2 hours to obtain a powdery catalyst composition containing 50 mol % Zr to Ca and the (Ca+Zr)/P mol ratio of 1.65. (Sample 66)

A solution obtained by dissolving 14.08 g of calcium nitrate $[Ca(NO_3)_2 \cdot 4H_2O]$ in 500 ml of distilled water and a solution obtained by dissolving 7.89 g of ammonium phosphate $[(NH_4)_2HPO_4]$ in 300 ml of distilled water were added dropwise to aqueous ammonia having adjusted pH of from 9 to 11 under a nitrogen atmosphere, and the mixture was stirred for one day.

Furthermore, solutions obtained by dissolving each of 7.23 g of zirconium (IV) chloride $(ZrCl_4)$ and 9.18 g of aluminum nitrate $[Al(NO_3)_3 \cdot 9H_2O]$ in 500 ml of distilled water respectively were added to the above-described mixture followed by further stirring for one day. Thereafter, the mixture was evaporated to dryness at 140° C. and after grinding, the ground product was burned at 700° C. for 2 hours to obtain a powdery catalyst composition containing 30 mol % Zr and 20 mol % Al to Ca and having the (Ca+Zr+Al)/P mol ratio of 2.00.

Comparative Sample 36

Comparative Sample 1 was used.

Comparative Sample 37

Comparative Sample 29 was used.

Comparative Sample 38

The calcium phosphate of Sample 48 was treated as the case of Sample 48 and burned in the air at 1200° C. for 2 hours to obtain a powdery catalyst composition.

Comparative Sample 39

Comparative Sample 4 was used.

Comparative Sample 40

Sample 48 was evaluated at a reaction temperature of 400° C.

Comparative Sample 41

The calcium phosphate of Sample 48 was treated as the case of Sample 48, burned in the air at 800° C. for 2 hours, and ground by a mortar to obtain a powder for the comparative sample.

Comparative Sample 42

Sample 55 was evaluated at a reaction temperature of 400° C.

Comparative Sample 43

The calcium phosphate of Sample 55 was treated as the case of Sample 55, burned in the air at 800° C. for 2 hours, and ground by a mortar to obtain a powder for the comparative sample.

Comparative Sample 44

Sample 2 was evaluated at a reaction temperature of 400° C.

Comparative Sample 45

The calcium phosphate of Sample 2 was treated as the case of Sample 2, burned in the air at 800° C. for 2 hours, and ground by a mortar to obtain a powder for the comparative sample.

Comparative Sample 46

Sepiolite (commercially available product) having a report of the synthesis example of 1,3-butadiene from ethanol was used.

Evaluation of Catalytic Characteristics

Each sample prepared in Samples 46 to 66 and Comparative samples 36 to 46 was formed to tablets of from #14 to #26. Then, the pretreatment was applied to the sample as the case of ethylene.

After finishing the pretreatment, the reaction was carried out under the conditions of a ethanol concentration of 20%, a carrier gas flow rate of 80 cc/minute (total flow rate 100 cc/min.) and a space velocity (GHSV) of 10,000 (l/h) at a normal pressure. In the case of the synthesis of 1,3-butadiene, the synthesis was carried out at a reaction temperature of from 450° C. to 700° C. The identification and the determination of the reaction gas were carried out by the same methods as the case of ethylene.

As the reaction apparatus, the gas flow-type catalytic reaction apparatus shown in FIG. 2 was used.

The evaluation results are shown in Table 5 and Table 6 below.

TABLE 5

EXAMPLES OF 1,3-BUTADIENE SYNTHESIS CATALYSTS

| | Composition | | | Characteristics | | | | |
|---|---|---|---|---|---|---|---|---|
| <Example> | (Ca + M)/P | Substituted metal | Substituted amount of metal (mol %) | Specific area (BET) (m²/g) | Reaction temperature (° C.) | Ethanol conversion (%) | Selectivity (%) | Space time yield (STY*) (g/h*L) |
| Sample 46 | 1.57 | none | | 27.4 | 500 | 88.3 | 6.2 | 137 |
| Sample 47 | 1.60 | none | | 2.6 | 700 | 100.0 | 14.4 | 359 |
| Sample 48 | 1.62 | none | | 26.7 | 600 | 100.0 | 15.5 | 387 |
| Sample 49 | 1.62 | none | | 26.7 | 550 | 98.5 | 24.1 | 592 |
| Sample 50 | 1.62 | none | | 26.7 | 500 | 86.9 | 34.6 | 750 |
| Sample 51 | 1.62 | none | | 26.7 | 450 | 55.4 | 32.5 | 449 |
| Sample 52 | 1.65 | none | | 36.4 | 500 | 91.9 | 23.4 | 536 |
| Sample 53 | 1.70 | none | | 37.4 | 500 | 89.7 | 9.2 | 206 |
| Sample 54 | 1.80 | none | | 35.2 | 550 | 94.3 | 6.6 | 155 |
| Sample 55 | 1.62 | Zr | 1 | 42.1 | 500 | 95.2 | 38.6 | 917 |
| Sample 56 | 1.62 | Zr | 1 | 42.1 | 450 | 74.1 | 37.1 | 686 |
| Sample 57 | 1.65 | Al | 0.1 | 37.2 | 550 | 98.2 | 35.2 | 862 |
| Sample 58 | 1.65 | Al | 0.1 | 37.2 | 500 | 93.6 | 47.6 | 1111 |
| Sample 59 | 1.65 | Al | 0.1 | 37.2 | 450 | 81.6 | 39.5 | 804 |
| Sample 60 | 1.65 | Ti | 3 | 48.2 | 450 | 84.7 | 37.3 | 788 |
| Sample 61 | 1.65 | W | 3 | 54.4 | 500 | 96.2 | 38.6 | 926 |
| Sample 62 | 1.65 | Zr | 3 | 52.9 | 500 | 89.6 | 43.7 | 977 |
| Sample 63 | 1.00 | Mg | 50 | 6.7 | 650 | 100.0 | 17.2 | 429 |
| Sample 64 | 1.50 | Mg | 30 | 73.1 | 450 | 65.1 | 14.7 | 239 |
| Sample 65 | 1.65 | Zr | 50 | 84.3 | 500 | 98.8 | 26.1 | 643 |
| Sample 66 | 2.00 | Zr, Al | 30, 20 | 23.5 | 600 | 100.0 | 12.5 | 312 |

TABLE 5-continued

EXAMPLES OF 1,3-BUTADIENE SYNTHESIS CATALYSTS

| | Composition | | | Characteristics | | | |
|---|---|---|---|---|---|---|---|
| <Example> | (Ca + M)/P | Substituted metal | Substituted amount of metal (mol %) | Specific area (BET) ($m^2/g$) | Reaction temperature (° C.) | Ethanol conversion (%) | Selectivity (%) | Space time yield (STY*) (g/h*L) |

<Reaction condition>: ethanol 20%, SV = 10,000 (1/h), 1 atm, V = 0.6 ml
*Space time yield (STY; $CH_2$ converted) ethanol flow rate (cc/h) × 0.7893/46.07 × 2 × 14 × ethanol conversion × selectivity/catalyst volume

TABLE 6

COMPARATIVE EXAMPLES OF 1,3-BUTADIENE SYNTHESIS CATALYSTS

| <Comparative Example> | (Ca + M)/P | Substituted metal | Substituted amount of metal (mol %) | Specific area (BET) ($m^2/g$) | Reaction temperature (° C.) | Ethanol conversion (%) | Selectivity (%) | Space time yield (STY*) (g/h*L) |
|---|---|---|---|---|---|---|---|---|
| Comparative sample 36 | 1.00 | none | | 5.6 | 550 | 37.8 | 0.0 | 0 |
| Comparative sample 37 | 1.50 | none | | 42.3 | 450 | 72.2 | 0.0 | 0 |
| Comparative sample 38 | 1.62 | none | | 0.8 | 650 | 65.6 | 9.7 | 159 |
| Comparative sample 39 | 2.00 | none | | 7.3 | 600 | 88.4 | 2.3 | 51 |
| Comparative sample 40 | 1.62 | none | | 26.7 | 400 | 27.2 | 17.4 | 118 |
| Comparative sample 41 | 1.62 | none | | 15.7 | 750 | 100.0 | 3.1 | 77 |
| Comparative sample 42 | 1.62 | Zr | 1 | 42.1 | 400 | 42.7 | 19.3 | 206 |
| Comparative sample 43 | 1.62 | Zr | 1 | 23.1 | 750 | 100.0 | 2.5 | 62 |
| Comparative sample 44 | 1.65 | Al | 0.1 | 37.2 | 400 | 40.3 | 20.6 | 207 |
| Comparative sample 45 | 1.65 | Al | 0.1 | 18.2 | 750 | 100.0 | 2.1 | 52 |
| Comparative sample 46 | | | | 131.6 | 500 | 73.7 | 3.1 | 57 |

<Reaction condition>: ethanol 20%, SV = 10,000 (1/h), 1 atm, V = 0.6 ml
*Space time yield (STY; $CH_2$ converted) ethanol flow rate (cc/h) × 0.7893/46.07 × 2 × 14 × ethanol conversion × selectivity/catalyst volume 6) Case of High-octane Fuel Synthesis Catalyst Preparation of Catalyst Sample 67

Comparative Sample 20 was used.

Sample 68

The calcium phosphate of Sample 48 was treated as the case of Sample 48, burned in the air at 1000° C. for 2 hours, and ground by a mortar to obtain a powder for the comparative sample.

Sample 69

Sample 48 was used.

Sample 70

Comparative Sample 3 was used.

Sample 71

Comparative Sample 3 was evaluated at a reaction temperature of 400° C.

Sample 72

Comparative Sample 3 was evaluated at a reaction temperature of 450° C.

Sample 73

Comparative Sample 3 was evaluated at a reaction temperature of 500° C.

Sample 74

Comparative Sample 3 was evaluated at a reaction temperature of 550° C.

Sample 75

Sample 53 was used.

Sample 76

Sample 37 was used.

Sample 77

A solution obtained by dissolving 228.0 of calcium nitrate [Ca $(NO_3)_2.4H_2O$] in 5.0 liters of distilled water and a solution obtained by dissolving 78.87 g of ammonium phosphate [(NH$_4$)$_2$HPO$_4$] in 3.0 liters of distilled water were added dropwise to aqueous ammonia having adjusted pH of from 9 to 11 under a nitrogen atmosphere, and the mixture was stirred for one day. Thereafter, the product was collected by filtration, washed with water, and dried at 140° C. to provide a powder having the Ca/P mol ratio of 1.62. After dissolving 0.007 g of lithium nitrate (LiNO$_3$) in 100 ml of distilled water, 10.0 g of the above-described calcium phosphate powder was added to the solution followed by stirring for one day. The mixture was dried at 140° C. and after grinding, was burned in the air at 700° C. for 2 hours to obtain a powdery catalyst composition containing 0.1 mol % Li to Ca and having the (Ca+Li)/P mol ratio of 1.62.

Sample 78

A solution obtained by dissolving 232.3 g of calcium nitrate [Ca(NO$_3$)$_2$.4H$_2$O] in 5.0 liters of distilled water and a solution obtained by dissolving 78.87 g of ammonium phosphate [(NH$_4$)$_2$HPO$_4$] in 3.0 liters of distilled water were added dropwise to aqueous ammonia having adjusted pH of from 9 to 11 under a nitrogen atmosphere, and the mixture was stirred for one day. Thereafter, the product was collected by filtration, washed with water, and dried at 140° C. to provide a powder having the Ca/P mol ratio of 1.65. After dissolving 0.029 g of nickel nitrate [Ni(NO$_3$)$_2$.6H$_2$O] in 100 ml of distilled water, 10.0 g of the above-described calcium phosphate powder was added to the solution followed by stirring for one day. The mixture was dried at 140° C. and after grinding, was burned in the air at 700° C. for 2 hours to obtain a powdery catalyst composition containing 0.1 mol % Ni to Ca and having the (Ca+Ni)/P mol ratio of 1.65.

Sample 79

After dissolving 0.202 g of lithium nitrate (LiNO$_3$) in 100 ml of distilled water, 9.98 g of the unburned calcium phosphate powder synthesized by Sample 48 was added to the solution followed by stirring for one day. The mixture was dried at 140° C. and after grinding, was burned in the air at 700° C. for 2 hours to obtain a powdery catalyst composition containing 3 mol % Li to Ca and having the (Ca+Li)/P mol ratio of 1.62.

Sample 80

Sample 79 was evaluated at a reaction temperature of 450° C.

Sample 81

Sample 79 was evaluated at a reaction temperature of 400° C.

Sample 82

After dissolving 0.838 g of nickel nitrate [Ni(NO$_3$)$_2$.6H$_2$O] in 100 ml of distilled water, 9.83 g of the unburned calcium phosphate synthesized by Sample 48 followed by stirring for one day. The mixture was dried at 140° C. and after grinding, was burned in the air at 700° C. for 2 hours to obtain a powdery catalyst composition containing 3 mol % Ni to Ca and having the (Ca+Ni)/P of 1.62.

Sample 83

After dissolving 0.854 g of nickel nitrate [Ni(NO$_3$)$_2$.6H$_2$O] in 100 ml of distilled water, 9.83 g of the unburned calcium phosphate synthesized by Comparative Sample 3 followed by stirring for one day. The mixture was dried at 140° C. and after grinding, was burned in the air at 1000° C. for 2 hours to obtain a powdery catalyst composition containing 3 mol % Ni to Ca and having the (Ca+Ni)/P of 1.65.

Sample 84

The Ni-containing calcium phosphate prepared in Sample 83 was treated as the case of Sample 83, burned in the air at 700° C. for 2 hours and ground by a mortar to obtained a catalyst composition.

Sample 85

Sample 84 was evaluated at a reaction temperature of 400° C.

Sample 86

After dissolving 0.871 g of zinc nitrate [Zn(NO$_3$)$_2$.6H$_2$O] in 100 ml of distilled water, 9.81 g of the unburned calcium phosphate powder synthesized by Comparative Sample 3 was added to the solution followed by stirring for one day. The mixture was dried at 140° C. and after grinding, was burned in the air at 700° C. for 2 hours to obtain a powdery catalyst composition containing 3 mol % Zn to Ca and having the (Ca+Zn)/P of 1.65.

Sample 87

After dissolving 0.837 g of titanium tetraisopropoxide {[(CH$_3$)$_2$CHO]$_4$Ti} in 100 ml of ethanol, 9.86 g of the unburned calcium phosphate powder synthesized by Comparative Example 3 was added to the solution followed by stirring for one day. The mixture was dried at 140° C., and after grinding, was burned in the air at 700° C. for 2 hours to obtain a powdery catalyst composition containing 3 mol % Ti to Ca and having the (Ca+Ti)/P mol ratio of 1.65.

Sample 88

After dissolving 0.616 g of strontium nitrate [Sr(NO$_3$)$_2$] in 100 ml of distilled water, 9.74 g of the unburned calcium phosphate powder synthesized by Comparative Example 3 was added to the solution followed by stirring for one day. The mixture was dried at 140° C., and after grinding, was burned in the air at 700° C. for 2 hours to obtain a powdery catalyst composition containing 3 mol % Sr to Ca and having the (Ca+Sr)/P mol ratio of 1.65.

Sample 89

After dissolving 1.274 g of europium nitrate [Eu(NO$_3$)$_3$.6H$_2$O] in 100 ml of distilled water, 9.56 g of the unburned calcium phosphate powder synthesized by Comparative Example 3 was added to the solution followed by stirring for one day. The mixture was dried at 140° C., and after grinding, was burned in the air at 700° C. for 2 hours to obtain a powdery catalyst composition containing 3 mol % Eu to Ca and having the (Ca+Eu)/P mol ratio of 1.65.

Sample 90

After dissolving 0.483 g of cesium chloride (CsCl) in 100 ml of distilled water, 9.61 g of the unburned calcium phosphate powder synthesized by Comparative Example 3 was added to the solution followed by stirring for one day. The mixture was dried at 140° C., and after grinding, was burned in the air at 700° C. for 2 hours to obtain a powdery catalyst composition containing 3 mol % Cs to Ca and having the (Ca+Cs)/P mol ratio of 1.65.

Sample 91

Sample 42 was used.

Sample 92

Sample 43 was used.

Sample 93

A solution obtained by dissolving 11.40 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 under a nitrogen atmosphere, and the mixture was stirred for one day. Furthermore, a solution obtained by dissolving 3.99 g of lithium nitrate ($LiNO_3$) in 500 ml of distilled water was added to the solution followed by further stirring for one day. Thereafter, the mixture was evaluated to dryness at 140° C. and after grinding, the ground product was burned in the air at 700° C. for 2 hours to obtain a powdery catalyst composition containing 50 mol % Li to Ca and having the (Ca+Li)/P mol ratio of 1.62.

Sample 94

A solution obtained by dissolving 11.61 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 under a nitrogen atmosphere, and the mixture was stirred for one day. Furthermore, a solution obtained by dissolving 13.09 g of nickel nitrate [$Ni(NO_3)_2 \cdot 6H_2O$] in 500 ml of distilled water was added to the solution followed by further stirring for one day. Thereafter, the mixture was evaluated to dryness at 140° C. and after grinding, the ground product was burned in the air at 700° C. for 2 hours to obtain a powdery catalyst composition containing 50 mol % Ni to Ca and having the (Ca+Ni)/P mol ratio of 1.65.

Sample 95

A solution obtained by dissolving 11.96 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 under a nitrogen atmosphere, and the mixture was stirred for one day. Furthermore, a solution obtained by dissolving 13.39 g of zinc nitrate [$Zn(NO_3)_2 \cdot 6H_2O$] in 500 ml of distilled water was added to the solution followed by further stirring for one day. Thereafter, the mixture was evaluated to dryness at 140° C. and after grinding, the ground product was burned in the air at 700° C. for 2 hours to obtain a powdery catalyst composition containing 50 mol % Zn to Ca and having the (Ca+Zn)/P mol ratio of 1.70.

Sample 96

A solution obtained by dissolving 14.08 g of calcium nitrate [$Ca(NO_3)_2 \cdot 4H_2O$] in 500 ml of distilled water and a solution obtained by dissolving 7.89 g of ammonium phosphate [$(NH_4)_2HPO_4$] in 300 ml of distilled water were added dropwise to aqueous ammonia having adjusted pH of from 9 to 11 under a nitrogen atmosphere, and the mixture was stirred for one day. Furthermore, solutions obtained by dissolving each of 9.85 g of nickel nitrate [$Ni(NO_3)_2 \cdot 6H_2O$] and 9.18 g of aluminum nitrate [$Al(NO_3)_3 \cdot 9H_2O$] in 500 ml of distilled water respectively were added to the solution followed by further stirring for one day. Thereafter, the mixture was evaluated to dryness at 140° C. and after grinding, the ground product was burned in the air at 700° C. for 2 hours to obtain a powdery catalyst composition containing 30 mol % Ni and 20 mol % Al to Ca and having the (Ca+Ni+Al)/P mol ratio of 2.00.

Comparative Sample 47

Comparative Sample 1 was used.

Comparative Sample 48

Comparative Sample 29 was used.

Comparative Sample 49

Comparative Sample 4 was used.

Comparative Sample 50

The calcium phosphate of Comparative Sample 3 was treated as the case of Comparative Sample 3, burned in the air at 1100° C. for 2 hours, and ground by a mortar to obtain a powder for the comparative sample.

Comparative Sample 51

Comparative Sample 3 was evaluated at a reaction temperature of 300° C.

Comparative Sample 52

The calcium phosphate of Comparative Sample 3 was treated as the case of Comparative Sample 3, burned in the air at 800° C. for 2 hours, and ground by a mortar to obtain a powder for the comparative sample.

Comparative Sample 53

The calcium phosphate of Sample 79 was treated as the case of Sample 79, burned in the air at 800° C. for 2 hours, and ground by a mortar to obtain a powder for the comparative sample.

Comparative Sample 54

The Ni-containing calcium phosphate prepared by Sample 82 was treated as the case of Sample 82, and burned in the air at 1200° C. for 2 hours to obtain a powdery catalyst comparative.

Comparative Sample 55

Sample 82 was evaluated at a reaction temperature of 250° C.

Comparative Sample 56

The Ni-containing calcium phosphate prepared by Sample 82 was treated as the case of Sample 82, and burned in the air at 800° C. for 2 hours to obtain a powdery catalyst comparative.

Comparative Sample 57

The Zn-containing calcium phosphate prepared by Sample 86 was treated as the case of Sample 86, and burned in the air at 800° C. for 2 hours to obtain a powdery catalyst comparative.

Comparative Sample 58

The Ti-containing calcium phosphate prepared by Sample 87 was treated as the case of Sample 87, and burned in the air at 800° C. for 2 hours to obtain a powdery catalyst comparative.

Comparative Sample 59

The Sr-containing calcium phosphate prepared by Sample 88 was treated as the case of Sample 88, and burned in the air at 800° C. for 2 hours to obtain a powdery catalyst comparative.

Comparative Sample 60

The Eu-containing calcium phosphate prepared by Sample 89 was treated as the case of Sample 89, and burned in the air at 800° C. for 2 hours to obtain a powdery catalyst comparative.

Comparative Sample 61

The Cs-containing calcium phosphate prepared by Sample 90 was treated as the case of Sample 90, and burned in the air at 800° C. for 2 hours to obtain a powdery catalyst comparative.

Comparative Sample 62

The Mg-containing calcium phosphate prepared by Sample 42 was treated as the case of Sample 42, and burned in the air at 800° C. for 2 hours to obtain a powdery catalyst comparative.

Comparative Sample 63

The Mg-containing calcium phosphate prepared by Sample 43 was treated as the case of Sample 43, and burned in the air at 800° C. for 2 hours to obtain a powdery catalyst comparative.

Comparative Sample 64

The Li-containing calcium phosphate prepared by Sample 93 was treated as the case of Sample 93, and burned in the air at 800° C. for 2 hours to obtain a powdery catalyst comparative.

Comparative Sample 65

The Ni-containing calcium phosphate prepared by Sample 94 was treated as the case of Sample 94, and burned in the air at 800° C. for 2 hours to obtain a powdery catalyst comparative.

Comparative Sample 66

The Zn-containing calcium phosphate prepared by Sample 95 was treated as the case of Sample 95, and burned in the air at 800° C. for 2 hours to obtain a powdery catalyst comparative.

Comparative Sample 67

The Ni,Al-containing calcium phosphate prepared by Sample 96 was treated as the case of Sample 96, and burned in the air at 800° C. for 2 hours to obtain a powdery catalyst comparative.

Evaluation of Catalytic Characteristics

Each sample prepared in Samples 67 to 96 and Comparative Samples 47 to 67 was formed to tablets of from #14 to #26. Then, the pretreatment was applied to the sample as the case of ethylene.

After finishing the pretreatment, the reaction was carried out under the conditions of a ethanol concentration of 20%, a methanol concentration of 20%, a carrier gas flow rate of 80 cc/minute (total flow rate 100 cc/min.) and a space velocity (GHSV) of 10,000 (1/h) at a normal pressure. In the case of the synthesis of high-octane fuel,. the synthesis was carried out at a reaction temperature of from 300° C. to 700° C. The identification and the determination of the reaction gas were carried out by the same methods as the case of ethylene. As the reaction apparatus, the gas flow-type catalytic reaction apparatus shown in FIG. 2 was used.

Evaluation results are shown in Table 7 and Table 8 below. In the tables, the liquid fraction is the reaction gas liquefied by a cooling pipe set to 0° C. The evaluation of the liquid fraction was carried out the evaluation method of JIS.

TABLE 7

EXAMPLES OF HIGH-OCTANE FUEL SYNTHESIS CATALYSTS

| | Composition | | | | Reaction characteristics | | |
|---|---|---|---|---|---|---|---|
| <Example> | (Ca + M)/P | Substituted metal | Substituted amount of metal (mol %) | Specific area (BET) ($m^2/g$) | Reaction temperature (° C.) | Ethanol conversion (%) | Liquid fraction Selectivity (%)*[2] |
| Sample 67 | 1.57 | none | | 27.4 | 500 | 88.3 | 36.2 |
| Sample 68 | 1.62 | none | | 3.8 | 700 | 100.0 | 45.8 |
| Sample 69 | 1.62 | none | | 26.7 | 500 | 86.9 | 76.2 |
| Sample 70 | 1.65 | none | | 36.4 | 350 | 18.6 | 96.2 |
| Sample 71 | 1.65 | none | | 36.4 | 400 | 32.1 | 95.3 |
| Sample 72 | 1.65 | none | | 36.4 | 450 | 57.9 | 92.8 |
| Sample 73 | 1.65 | none | | 36.4 | 500 | 91.9 | 86.1 |
| Sample 74 | 1.65 | none | | 36.4 | 550 | 99.1 | 82.5 |
| Sample 75 | 1.70 | none | | 37.4 | 450 | 55.7 | 87.6 |
| Sample 76 | 1.80 | none | | 35.2 | 500 | 84.3 | 67.8 |
| Sample 77 | 1.62 | Li | 0.1 | 27.1 | 500 | 80.6 | 72.6 |
| Sample 78 | 1.65 | Ni | 0.1 | 37.6 | 450 | 60.6 | 93.4 |
| Sample 79 | 1.62 | Li | 3 | 40.2 | 500 | 87.4 | 86.9 |
| Sample 80 | 1.62 | Li | 3 | 40.2 | 450 | 60.8 | 88.6 |
| Sample 81 | 1.62 | Li | 3 | 40.2 | 400 | 37.2 | 94.2 |
| Sample 82 | 1.62 | Ni | 3 | 41.8 | 500 | 96.7 | 81.7 |
| Sample 83 | 1.65 | Ni | 3 | 2.8 | 650 | 100.0 | 65.2 |
| Sample 84 | 1.65 | Ni | 3 | 47.1 | 450 | 79.2 | 86.2 |
| Sample 85 | 1.65 | Ni | 3 | 47.1 | 400 | 46.8 | 92.7 |
| Sample 86 | 1.65 | Zn | 3 | 52.3 | 450 | 86.5 | 84.2 |
| Sample 87 | 1.65 | Ti | 3 | 45.9 | 450 | 68.5 | 83.1 |
| Sample 88 | 1.65 | Sr | 3 | 38.2 | 500 | 85.3 | 90.6 |

TABLE 7-continued

EXAMPLES OF HIGH-OCTANE FUEL SYNTHESIS CATALYSTS

| | | | | | | | |
|---|---|---|---|---|---|---|---|
| Sample 89 | 1.65 | Eu | 3 | 36.8 | 450 | 59.2 | 93.4 |
| Sample 90 | 1.65 | Cs | 3 | 40.5 | 550 | 93.1 | 90.4 |
| Sample 91 | 1.00 | Mg | 50 | 6.7 | 600 | 85.3 | 62.4 |
| Sample 92 | 1.50 | Mg | 30 | 73.1 | 350 | 53.2 | 72.5 |
| Sample 93 | 1.62 | Li | 50 | 56.8 | 450 | 88.1 | 68.8. |
| Sample 94 | 1.65 | Ni | 50 | 68.4 | 300 | 47.8 | 88.6 |
| Sample 95 | 1.70 | Zn | 50 | 71.3 | 400 | 62.5 | 81.1 |
| Sample 96 | 2.00 | Ni, Al | 30, 20 | 19.6 | 600 | 98.9 | 60.3 |

| | Fuel characteristics | | | |
|---|---|---|---|---|
| <Example> | Oxygen-containing HC ratio (wt)*3 | Space time yield* (g/h*L) | Ethanol content in fuel (%)*4 | Distillation property Initial boiling point/end point (° C.) |
| Sample 67 | 43 | 903 | 32 | |
| Sample 68 | 18 | 1142 | 0 | |
| Sample 69 | 26 | 1901 | 17 | |
| Sample 70 | 94 | 2400 | 85 | |
| Sample 71 | 80 | 2377 | 71 | 70/176 |
| Sample 72 | 64 | 2315 | 45 | 68/192 |
| Sample 73 | 29 | 2148 | 9 | 54/206 |
| Sample 74 | 4 | 2057 | 1 | |
| Sample 75 | 68 | 2185 | 51 | |
| Sample 76 | 37 | 1691 | 23 | |
| Sample 77 | 42 | 1811 | 27 | |
| Sample 78 | 58 | 2330 | 42 | |
| Sample 79 | 35 | 2168 | 14 | |
| Sample 80 | 59 | 2210 | 44 | |
| Sample 81 | 76 | 2350 | 67 | |
| Sample 82 | 18 | 2038 | 4 | |
| Sample 83 | 29 | 1626 | 0 | |
| Sample 84 | 41 | 2150 | 24 | |
| Sample 85 | 72 | 2312 | 57 | |
| Sample 86 | 29 | 2100 | 16 | |
| Sample 87 | 47 | 2073 | 38 | |
| Sample 88 | 32 | 2260 | 16 | |
| Sample 89 | 58 | 2330 | 44 | |
| Sample 90 | 26 | 2255 | 8 | |
| Sample 91 | 41 | 1557 | 24 | |
| Sample 92 | 70 | 1809 | 65 | |
| Sample 93 | 26 | 1716 | 17 | |
| Sample 94 | 77 | 2210 | 59 | |
| Sample 95 | 64 | 2023 | 46 | |
| Sample 96 | 16 | 1504 | 2 | |

<Reaction condition>: ethanol 20%, SV = 10,000 (1/h), 1 atm, V = 0.6 ml
(Marks * are described in Table 8)

TABLE 8

COMPARATIVE EXAMPLES OF HIGH-OCTANE FUEL SYNTHESIS CATALYSTS

| | Composition | | | | Reaction characteristics | | | | Fuel characteristics | |
|---|---|---|---|---|---|---|---|---|---|---|
| <Example> | (Ca + M)/P | Substituted metal | Substituted amount of metal (mol %) | Specific area (BET) (m²/g) | Reaction temperature (° C.) | Ethanol conversion (%) | Liquid fraction Selectivity(%)*2 | Oxygen-containing HC ratio (wt)*3 | Space time yield* (g/h*L) | Ethanol content in fuel (%)*4 |
| Comparative sample 47 | 1.00 | none | | 5.6 | 500 | 25.8 | rest ethanol only | | | 100 |
| Comparative sample 48 | 1.50 | none | | 42.3 | 500 | 86.2 | rest ethanol only | | | 100 |
| Comparative sample 49 | 2.00 | none | | 7.3 | 500 | 32.4 | 71.6 | >85% ethanol | 1786 | 94 |
| Comparative sample 50 | 1.65 | none | | 1.2 | 500 | 21.7 | 86.3 | >85% ethanol | 2153 | 91 |
| Comparative sample 51 | 1.65 | none | | 36.4 | 300 | 6.2 | 97.6 | >85% ethanol | 2435 | 96 |
| Comparative sample 52 | 1.65 | none | | 16.7 | 750 | 100.0 | 17.6 | 16 | 439 | 0 |
| Comparative sample 53 | 1.62 | Li | 3 | 20.1 | 750 | 100.0 | 15.3 | 13 | 382 | 0 |

TABLE 8-continued

COMPARATIVE EXAMPLES OF HIGH-OCTANE FUEL SYNTHESIS CATALYSTS

| | Composition | | | | Reaction characteristics | | | | Fuel characteristics | |
|---|---|---|---|---|---|---|---|---|---|---|
| <Example> | (Ca + M)/P | Substituted metal | Substituted amount of metal (mol %) | Specific area (BET) (m²/g) | Reaction temperature (° C.) | Ethanol conversion (%) | Liquid fraction Selectivity(%)*² | Oxygen-containing HC ratio (wt)*³ | Space time yield* (g/h*L) | Ethanol content in fuel (%)*⁴ |
| Comparative sample 54 | 1.62 | Ni | 3 | 0.8 | 500 | 26.4 | 83.2 | >85% ethanol | 2075 | 88 |
| Comparative sample 55 | 1.62 | Ni | 3 | 41.8 | 250 | 11.8 | 94.5 | >85% ethanol | 2357 | 93 |
| Comparative sample 56 | 1.62 | Ni | 3 | 21.6 | 750 | 100.0 | 11.8 | 7 | 294 | 0 |
| Comparative sample 57 | 1.65 | Zn | 3 | 26.3 | 750 | 100.0 | 22.7 | 5 | 566 | 0 |
| Comparative sample 58 | 1.65 | Ti | 3 | 24.7 | 750 | 100.0 | 8.2 | 6 | 205 | 0 |
| Comparative sample 59 | 1.65 | Sr | 3 | 18.6 | 750 | 100.0 | 15.6 | 8 | 389 | 0 |
| Comparative sample 60 | 1.65 | Eu | 3 | 16.2 | 750 | 100.0 | 13.1 | 7 | 327 | 0 |
| Comparative sample 61 | 1.65 | Cs | 3 | 20.9 | 750 | 100.0 | 15.2 | 6 | 379 | 0 |
| Comparative sample 62 | 1.00 | Mg | 50 | 4.3 | 750 | 100.0 | 15.7 | 9 | 392 | 0 |
| Comparative sample 63 | 1.50 | Mg | 30 | 34.8 | 750 | 100.0 | 18.3 | 11 | 456 | 0 |
| Comparative sample 64 | 1.62 | Li | 50 | 28.1 | 750 | 100.0 | 16.5 | 10 | 412 | 0 |
| Comparative sample 65 | 1.65 | Ni | 50 | 31.2 | 750 | 100.0 | 17.9 | 12 | 447 | 0 |
| Comparative sample 66 | 1.70 | Zn | 50 | 32.7 | 750 | 100.0 | 18.4 | 15 | 459 | 0 |
| Comparative sample 67 | 2.00 | Ni, Al | 30, 20 | 19.6 | 750 | 100.0 | 15.2 | 21 | 379 | 0 |

<Reaction condition>: ethanol 20%, SV = 10,000 (1/h), 1 atm, V = 0.6 ml
*Space time yield (STY; $CH_2$ converted) ethanol flow rate (cc/h) × 0.7893/46.07 × 2 × 14 × ethanol conversion × selectivity/catalyst volume
*²Liquid fraction contains 1,3-butadiene and 1-butanol
*³Ratio of oxygen-containing hydrocarbons in liquid fraction
*⁴Because when content of ethanol in fuel is large, starting property and running distance are lowered as compared with gasoline, the synthesis of the fuel becomes meaningless.

As an example of the composition analysis of the liquid fraction, the analytical results of Sample 73 are shown below. The main components were oxygen-containing hydrocarbon compounds and the contents were as follows.

Ethanol=10% (unreacted ethanol), $C_4H_{10}$=6%, $C_4H_8O$=4%, $C_5H_{10}O$=3%, $C_6H_{14}O$=2%, $C_6H_{10}$=5%, aromatic =8% other hydrocarbons.

The components of other liquid fractions formed by the reactions used the catalysts of the examples were almost same as those of Sample 73 but the contents of the components in the fuels were different by the kind of the catalyst and the reaction temperatures.

After operating 12 hours using 0.6 ml of the tablets of #14 to #26 formed by Sample 73, under the conditions of a reaction temperature of 500° C., an ethanol concentration of 20%, a space velocity (GHSV) of 10,000 (l/h), a supplying mixed gas total flow rate of 100 cc/min., and a normal pressure, the catalyst was treated in a 2% oxygen atmosphere at 480° C. for 15 minutes as a catalyst regeneration treatment, the catalyst was successively used under the same conditions (500° C., EtOH concentration=20%, GHSV=10,000 (l/h), and V=0.6 ml), the conversion of ethanol was measured, whereby the stability of the catalyst activity with the passage of time was measured. The result is shown in FIG. 3. The result shows that by a periodical catalyst activity treatment, the catalyst activity is completely maintained.

INDUSTRIAL APPLICABILITY the catalyst of the present invention can be easily produced, is stable, and can efficiently obtain desired substances from ethanol by selecting the Ca/p mol ratio of the catalyst, the activating metal, and a reaction temperature according to the desired substances without lowering the activity even in the existence of water.

What is claimed is:

1. A method of synthesizing 1-butanol, characterized in that ethanol is brought into contact with low-crystalline calcium phosphate having a specific area of at least 2 m²/g and the Ca/P mol ratio of from 1.6 to 1.8 at a temperature range of from 350° C. to 450° C.

2. A method of synthesizing 1,3-butadiene, characterized in that ethanol is brought into contact with low-crystalline calcium phosphate having a specific area of at least 2 m²/g and the Ca/P mol ratio of from 1.55 to 1.8 at a temperature range of from 450° C. to 700° C.

3. A method of synthesizing a high-octane fuel, characterized in that ethanol is brought into contact with low-crystalline calcium phosphate having a specific area of at least 2 m²/g and the Ca/P mol ratio of from 1.55 to 1.8 at a temperature range of from 300° C. to 700° C.

4. A method of synthesizing 1-butanol, characterized in that ethanol is brought into contact with low-crystalline calcium phosphate having thereon at least one kind of a metal and/or the metal oxide selected from Ba, Na, K, Li, Cs, Sr, Y, Ce, Sb, Eu, Ti, W, and Zr in an amount of not more than 50 mol % to Ca, and having a specific area of at least 2 m$^2$/g and the (Ca+metal)/P mol ratio of from 1 to 2 at a temperature range of from 300° C. to 450° C.

* * * * *